(12) United States Patent
Pettit et al.

(10) Patent No.: US 7,507,851 B2
(45) Date of Patent: Mar. 24, 2009

(54) HALOCOMBSTATINS AND METHODS OF SYNTHESIS THEREOF

(75) Inventors: George R. Pettit, Paradise Valley, AZ (US); Mathew D. Minardi, Mather, CA (US); Heidi J. Rosenberg, Tempe, AZ (US)

(73) Assignee: Arizona Board of Regents, a state corporate of the State of Arizona, acting for and on behalf of Arizona State University, Tempe, AZ (US)

( * ) Notice: Subject to any disclaimer, the term of this patent is extended or adjusted under 35 U.S.C. 154(b) by 0 days.

(21) Appl. No.: 12/021,246

(22) Filed: Jan. 28, 2008

(65) Prior Publication Data

US 2008/0119649 A1    May 22, 2008

Related U.S. Application Data

(63) Continuation of application No. 11/690,799, filed on Mar. 23, 2007, now abandoned, which is a continuation of application No. 10/948,926, filed on Sep. 24, 2004, now Pat. No. 7,223,747.

(60) Provisional application No. 60/505,935, filed on Sep. 24, 2003.

(51) Int. Cl.
  *A61K 31/661* (2006.01)
  *C07F 9/09* (2006.01)
(52) U.S. Cl. ............... 558/210; 514/147; 514/140; 514/141
(58) Field of Classification Search ............ 558/210; 514/147
See application file for complete search history.

(56) References Cited

U.S. PATENT DOCUMENTS

| | | | | |
|---|---|---|---|---|
| 5,561,122 | A * | 10/1996 | Pettit | 514/130 |
| 6,919,324 | B2 * | 7/2005 | Chaplin et al. | 514/114 |
| 7,223,747 | B2 * | 5/2007 | Pettit et al. | 154/145 |
| 2004/0152629 | A1 * | 8/2004 | Hadfield et al. | 514/12 |
| 2004/0209951 | A1 * | 10/2004 | Gokaraju et al. | 514/543 |

FOREIGN PATENT DOCUMENTS

WO    WO 200250007 A2 *    6/2002

OTHER PUBLICATIONS

Lawrence, N. J., "Synthesis and Anticancer Activity of Fluorinated Analogues of Combretastatin A-4", *J. Fluorine Chem*, 123(1):101-108 (2003).*
International Search Report for PCT/US2005/033998 dated Mar. 3, 2006.*
Written Opinion of the International Searching Authority for PCT/US2005/033998 dated Mar. 3, 2006.*
International Preliminary Report on Patentability for PCT/US2005/033998 dated Mar. 27, 2007.*

* cited by examiner

*Primary Examiner*—Rebecca L Anderson
*Assistant Examiner*—Jason M Nolan
(74) *Attorney, Agent, or Firm*—Fennemore Craig, P.C.

(57) ABSTRACT

The invention relates to novel compounds denominated halocombstatins. The halocombstatins are derivatives of combretastatin A-3, and include compounds that exhibit cancer growth cell inhibition against a panel of human cancer cell lines and the murine P388 leukemia, as well as activity as inhibitors of tubulin polymerization and inhibitors of the binding of colchicine to tubulin.

12 Claims, 11 Drawing Sheets

1a, R = H, combretastatin A-4
b, R = $PO_3Na_2$

2a, R = H, combretastatin A-2
b, R = $PO_3Na_2$

3a, R = H, combretastatin A-3
b, R = $PO_3Na_2$

HALOCOMBSTATINS AND METHODS OF SYNTHESIS THEREOF

RELATED APPLICATION DATA

This application is a continuation of U.S. Nonprovisional patent application Ser. No. 11/690,799 filed on Mar. 23, 2007, which is a continuation of U.S. Nonprovisional patent application Ser. No. 10/948,926 filed on Sep. 24, 2004 (now U.S. Pat. No. 7,223,747), which is based on and claims the benefit of U.S. Provisional Patent Application No. 60/505,935 filed on Sep. 24, 2003, the disclosure of which is incorporated herein in its entirety by this reference.

Financial assistance for this invention was provided by the United States Government, Division of Cancer Treatment and Diagnosis, National Cancer Institute, Department of Health and Human Services Outstanding Investigator Grant Numbers CA44344-05-12; R01-CA90441-01; and R01 CA090441-03-041; the Arizona Disease Control Research Commission contract Number 9815; and private contributions. Thus, the United States Government has certain rights in this invention.

FIELD OF THE INVENTION

This invention relates to novel compounds having utility in the treatment of cancer and/or as antimicrobials.

BACKGROUND OF THE INVENTION

Pharmaceutical agents to treat cancer and/or tumors are widely sought. Antiangiogenesis agents are being pursued as a promising antitumor therapeutic agents. Combretastatin A-4 is one such antiangiogenesis agent. Studies have demonstrated that combretastatin A-4 disrupts the microtubules of human umbilical vein endothelial cells (HUVEC) in culture. It has also been shown that the tubulin-binding properties shown in cell-free systems are retained when the compound enters cells, and that tubulin binding is a significant component of biological activity.

The African Bush Willow *Combretum caffrum* has proved to be a very important source of cancer cell growth inhibitory constituents named combretastatins. The most potent of these constituents is combretastatin A-4 (1a, "CA-4"), and its sodium phosphate derivative (1b, "CA-4P") was advanced to Phase I human cancer clinical trials in 1998. (Remick, S. C., et al., (1999) Phase I Pharmacokinetics Study of Single Dose Intravenous (IV) Combretastatin A-4 Prodrug (CA4P) in Patients (pts) with Advanced Cancer, *Molecular Targets and Cancer Therapeutics Discovery Discovery, Development, and Clinical Validation*, Proceedings of the AACR-NCI-EORTC International Congress, Washington, D.C., #16, p. 4.) Overall results continue to be promising, and human cancer Phase II and combination Ib trials are currently underway.

Antivascular, antiangiogenesis and general antimetastatic activities of CA4P as well as its synergistic utility in combination with other anticancer drugs, radioimmunotherapy and hyperthermia are all areas of active research interest. (see Griggs, J., et al., Combretastatin A-4 Disrupts Neovascular Development in Non-Neoplastic Tissue, *British J. of Cancer* 2001, 84, 832-835; Folkman, J., Angiogenesis-Dependent Diseases, *Seminars in Oncology* 2001, 28, 536-542; Kruger, E. A. et al., Approaches to Preclinical Screening of Antiangiogenic Agents, *Seminars in Oncology* 2001, 28, 570-576; Jin, X., et al., Evaluation of Endostatin Antiangiogenesis Gene Therapy in vitro and in vivo, *Cancer Gene Therapy* 2001, 8, 982-989; Vacca, A., et al., Bone Marrow Angiogenesis in Patients with Active Multiple Myeloma, *Seminars in Oncology* 2001, 28, 543-550; Rajkumar, S. V., et al., Angiogenesis in Multiple Myeloma, *Seminars in Oncology* 2001, 28, 560-564, Griggs, J., et al., Potent Anti-metastatic Activity of Combretastatin A-4, *Int. J. Oncol.* 2001, 821-825; Pedley, R. B. et al., Eradication of Colorectal Xenografts by Combined Radioimmunotherapy and Combretastatin A-4 3—O-Phosphate, *Cancer Research* 2001, 61, 4716-4722; Eikesdal, H. P., et al., Tumor Vasculature is Targeted by the Combination of Combretastatin A-4 and Hyperthermia, *Radiotherapy and Oncology* 2001, 61, 313-320.)

Several of the compounds of the present invention are particularly concerned with treatment of thyroid gland cancer. By 2002, some 20,000 people in the United States were diagnosed with carcinoma of the thyroid gland; of these the distribution was about 80% papillary and 14% follicular differentiated carcinomas derived from follicular epithelial cells producing thyroid hormone. Of the remaining thyroid malignancies, about 4% were medullary carcinoma (neuroendocrine) and 2% of the exceptionally aggressive anaplastic carcinoma (median survival 4-5 months and a near 100% lethal outcome). Significantly, the incidence of both follicular and anaplastic carcinomas are elevated in geographic areas of iodine deficiency. Radiation exposure represents the most general risk factor for thyroid cancer. In addition, excess production of the pituitary hormone thyroid-stimulating hormone (THS), which is very important in regulating thyroid gland growth and function, may be important in the etiology of thyroid cancer. Previously used clinical treatments for thyroid cancer include surgery, suppression of THS, $^{131}$I-radiotherapy, and anticancer drugs. But in 2002, another 1,300 victims of thyroid cancer in the U.S. died, emphasizing the great need for more routinely effective anticancer drugs.

SUMMARY OF THE INVENTION

The present invention relates to novel compounds constituting modifications of combretastatin A-3 (3a) and its phosphate prodrug (3b), wherein the 3-hydroxy group or the 3-hydroxy and 5-hydroxy groups are replaced with a halide. Representative halides are fluorine, chlorine, bromine and iodine. Salts of the novel compounds are also disclosed herein. Also described herein are phosphate ester derivatives of the 3-fluoro, 3-chloro, 3-bromo and 3-iodo-stilbenes.

Compounds of the invention comprise:

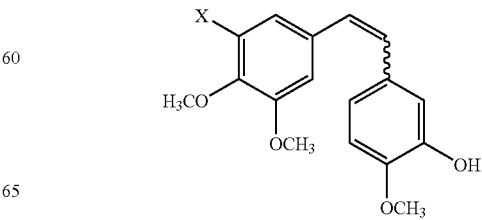

Wherein X is F, Cl, Br or I

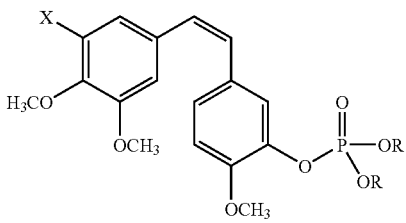

Wherein X is F, Cl, Br or I, and R is a metal cation such as Na, Li, K, Cs, Rb, Ca, Mg or is morpholine, piperidine, glycine-$OCH_3$, tryptophan-$OCH_3$ or $NH(CH_2OH)_3$.

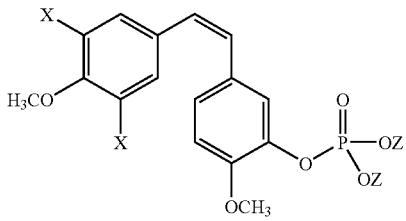

Wherein X is F, Cl, Br or I, and Z is a metal cation such as Na, Li, K, Cs, Rb, Ca, Mg or is morpholine, piperidine, glycine-$OCH_3$, trytophan-$OCH_3$ or $NH(CH_2OH)_3$.

Several of the compounds of the invention exhibit greatly enhanced (>10-100×) cancer cell growth inhibition, as compared to prior art combretastatin compounds such as CA-4 and CA-3, against a panel of human cancer cell lines and the murine P388 leukemia. The iodo compounds appear to show particular promise in the treatment of thyroid cancers. The compounds of the present invention exhibit inhibiting of tubulin polymerization and binding of colchicine to tubulin. In addition several of the compounds exhibit antimicrobial properties.

DETAILED DESCRIPTION OF THE INVENTION

Figure 1:
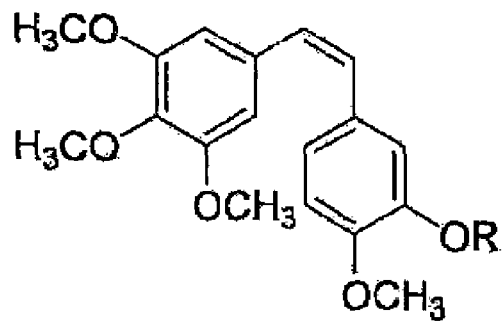
FIG. 1 shows the structural formulas of several prior art compounds.
Figure 1:
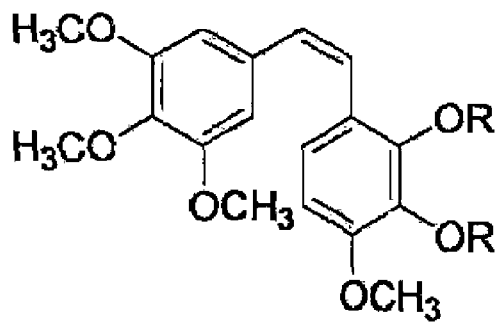
Figure 1:
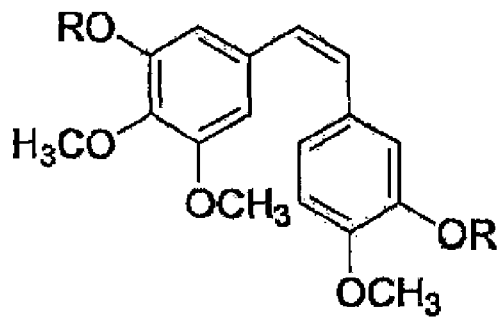
Figure 2:
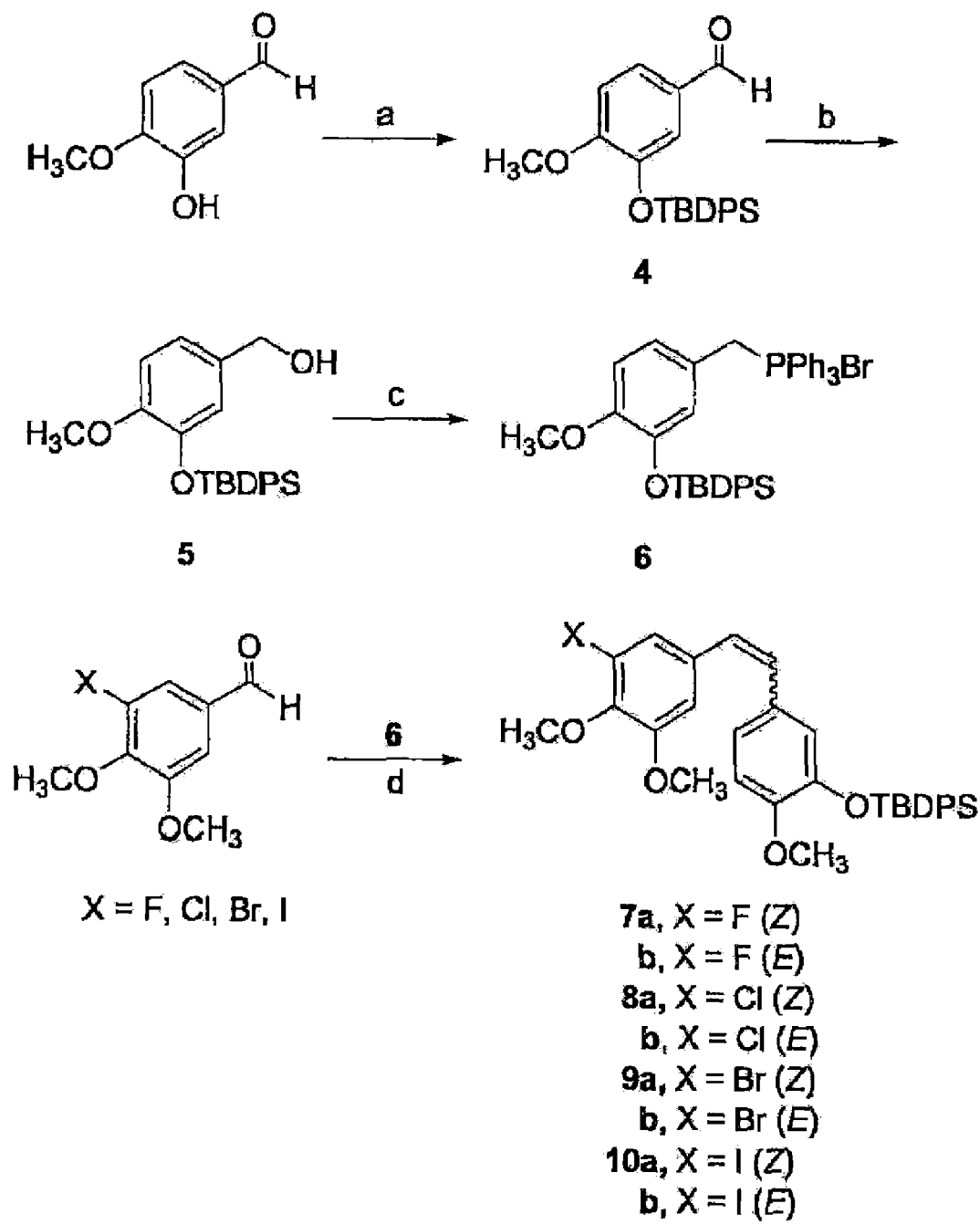
FIG. 2 shows the reaction scheme for synthesizing some of the compounds of the present invention, including structural formulas for the compounds of the invention.
Figure 3:
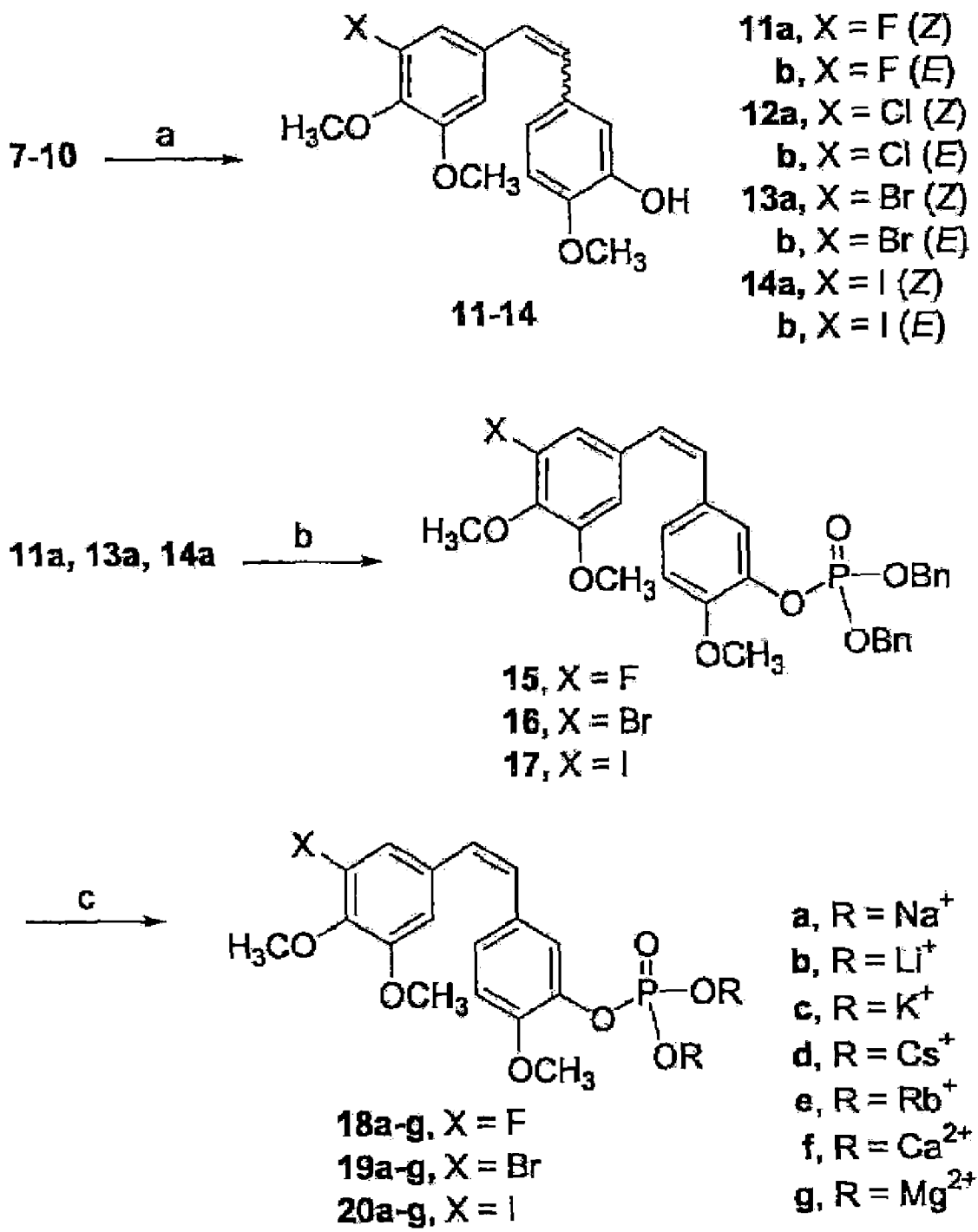
FIG. 3 shows a continuation of the reaction scheme of FIG. 2.
Figure 4:
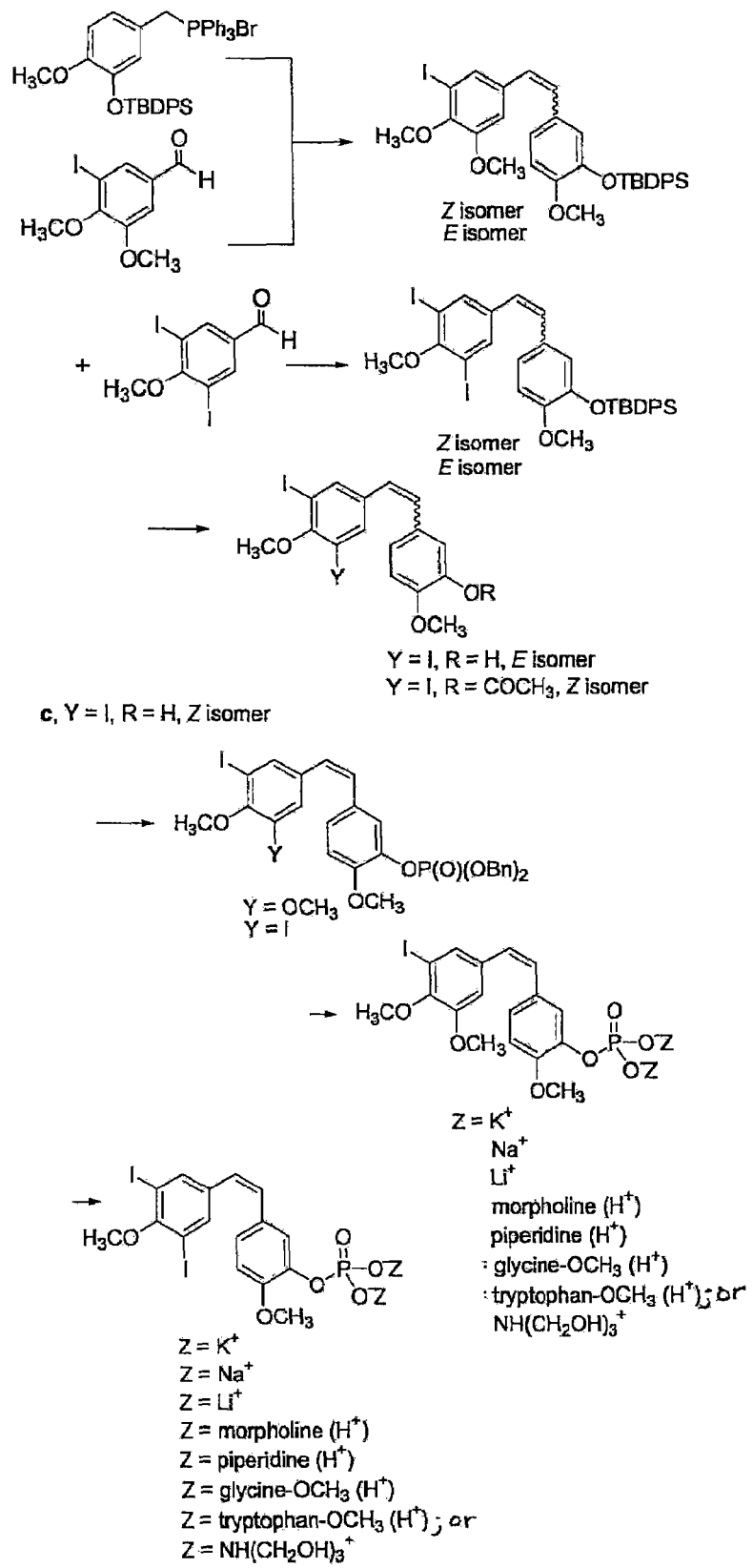
FIG. 4 shows the reaction scheme for synthesizing some of the compounds of the present invention, including structural formulas for the compounds of the invention.
Figure 5A:
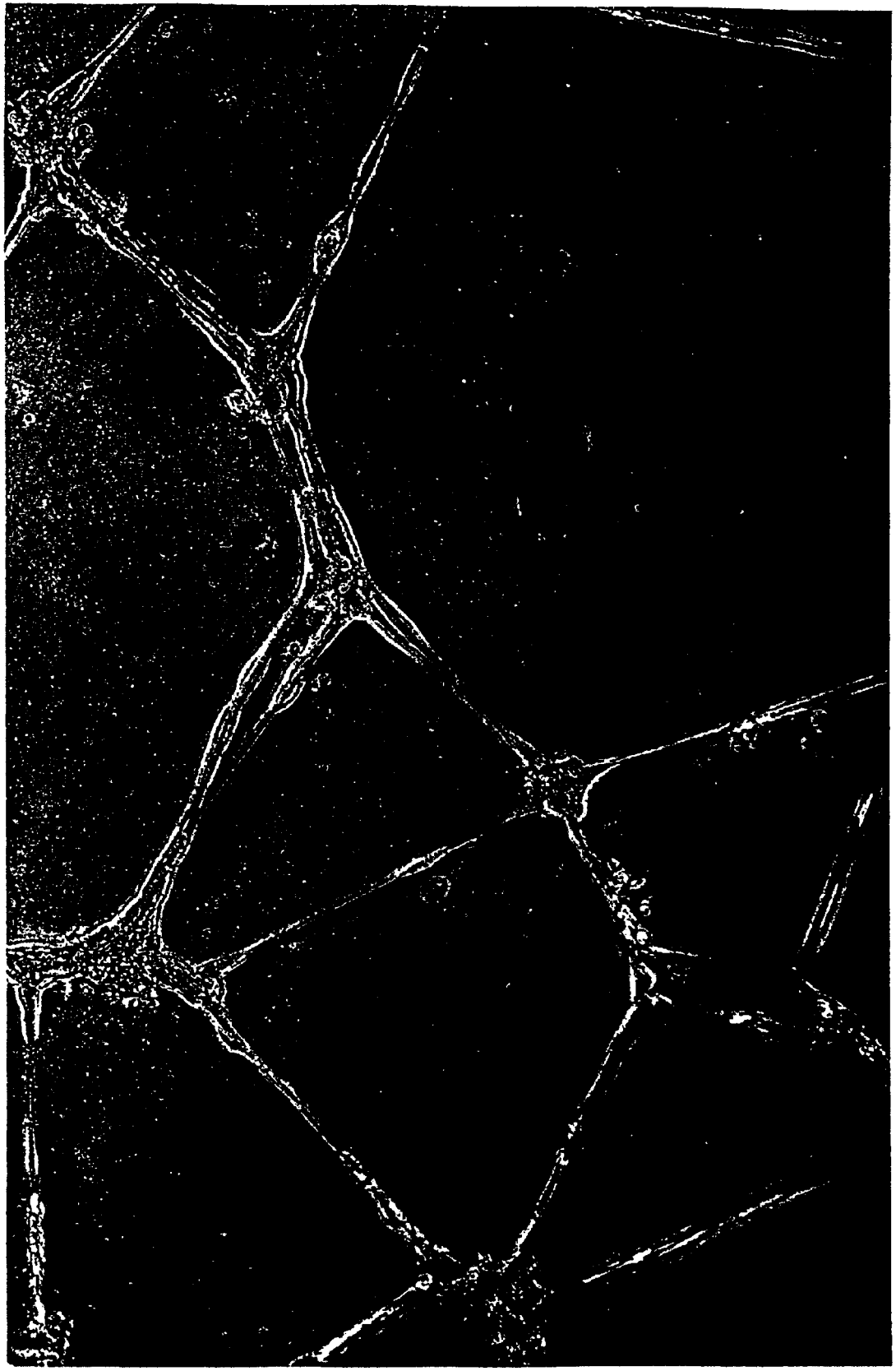
FIG. 5 shows photographs of results of the cord formation assay.
Figure 5B:
Figure 5C:
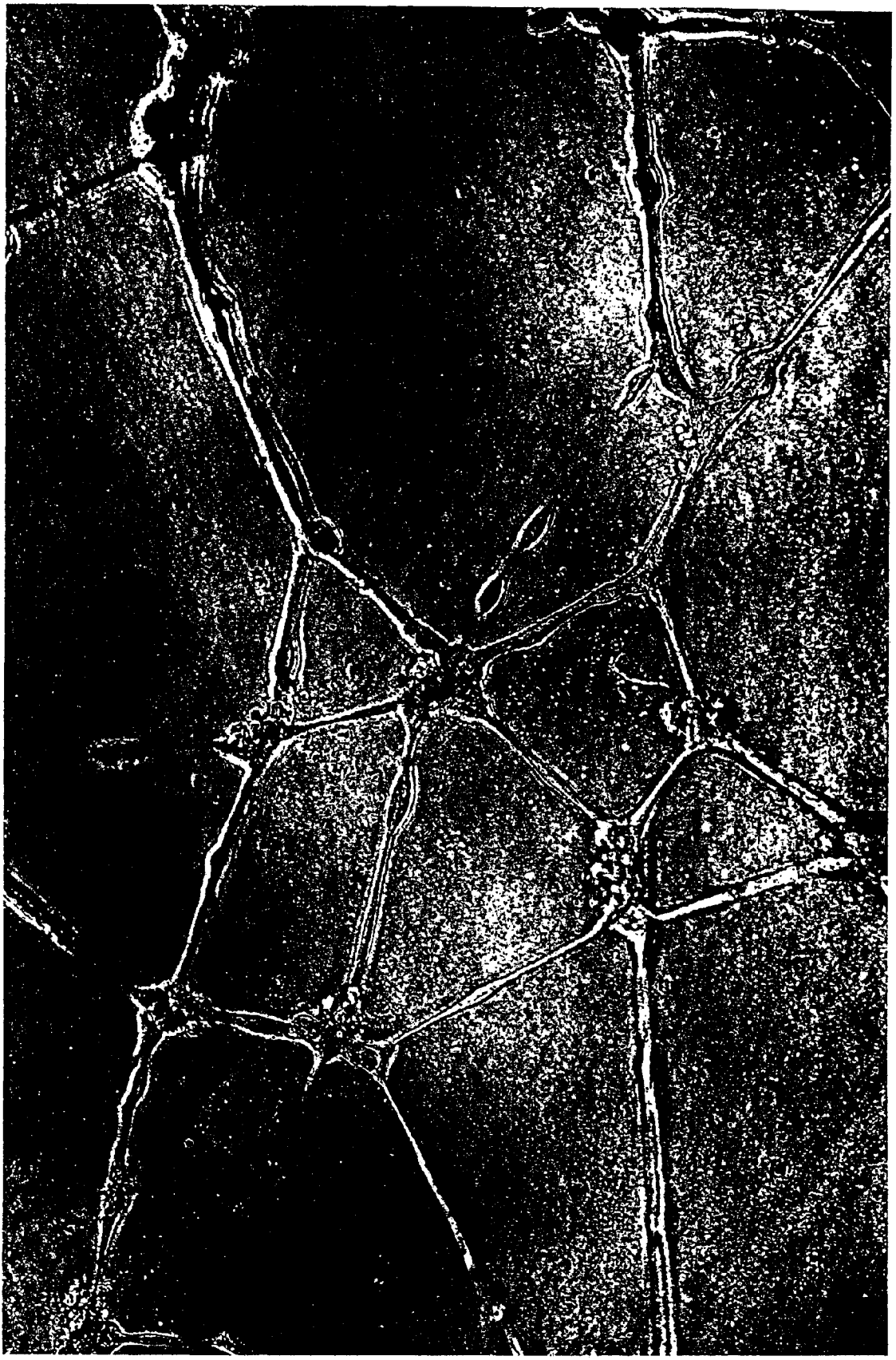
Figure 5D:
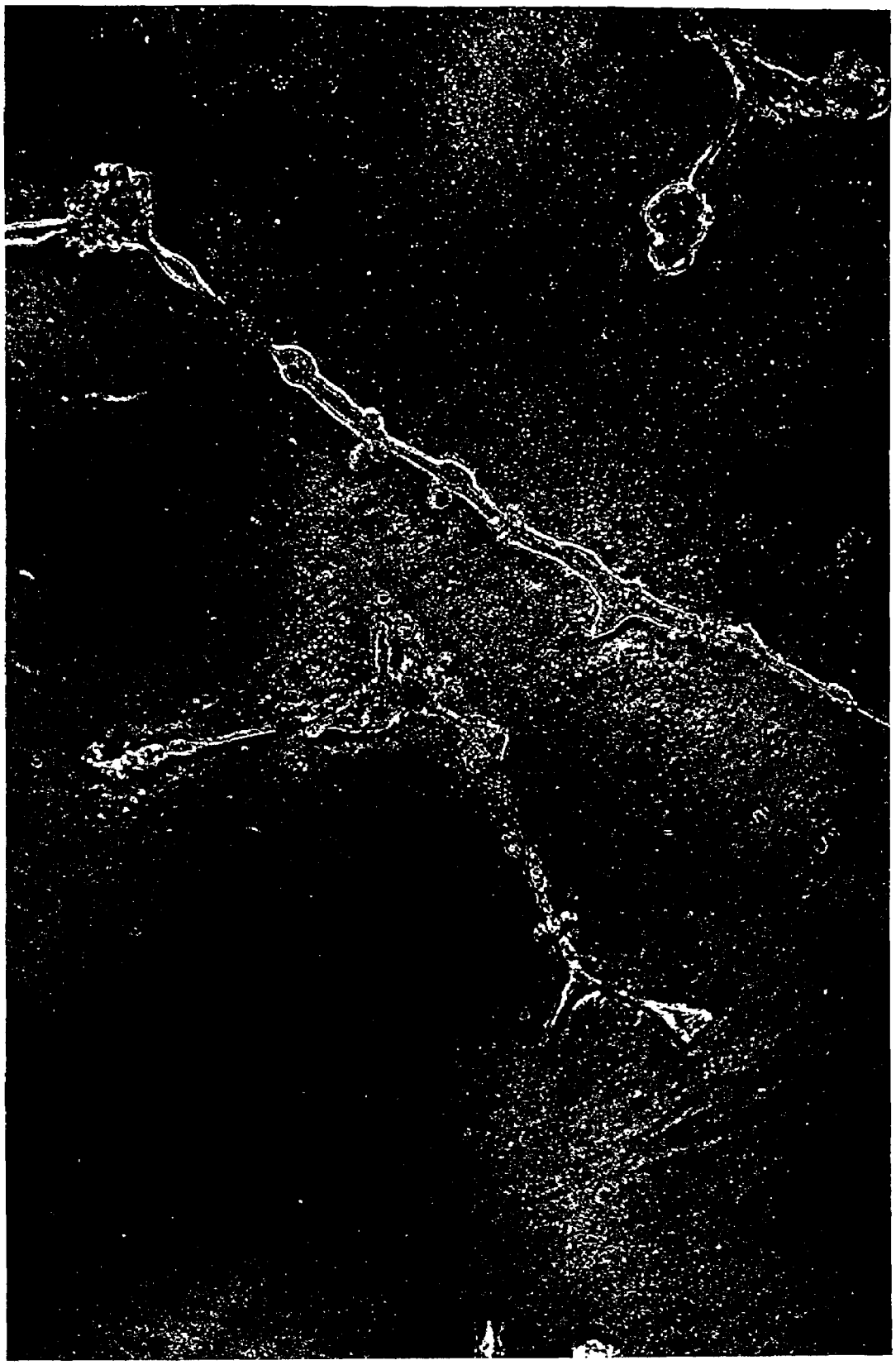
Figure 5E:
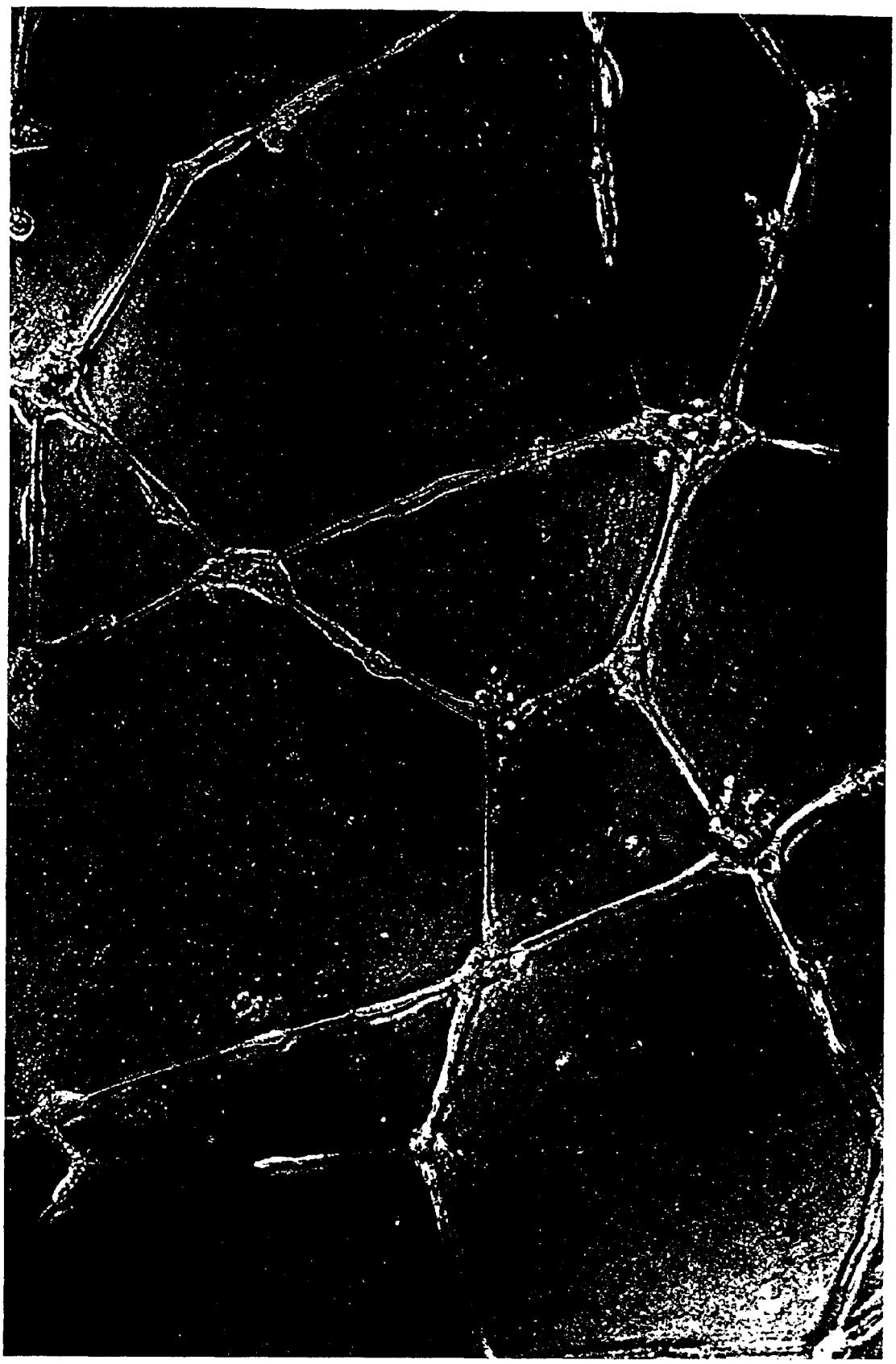
Figure 5F:
Figure 5G:
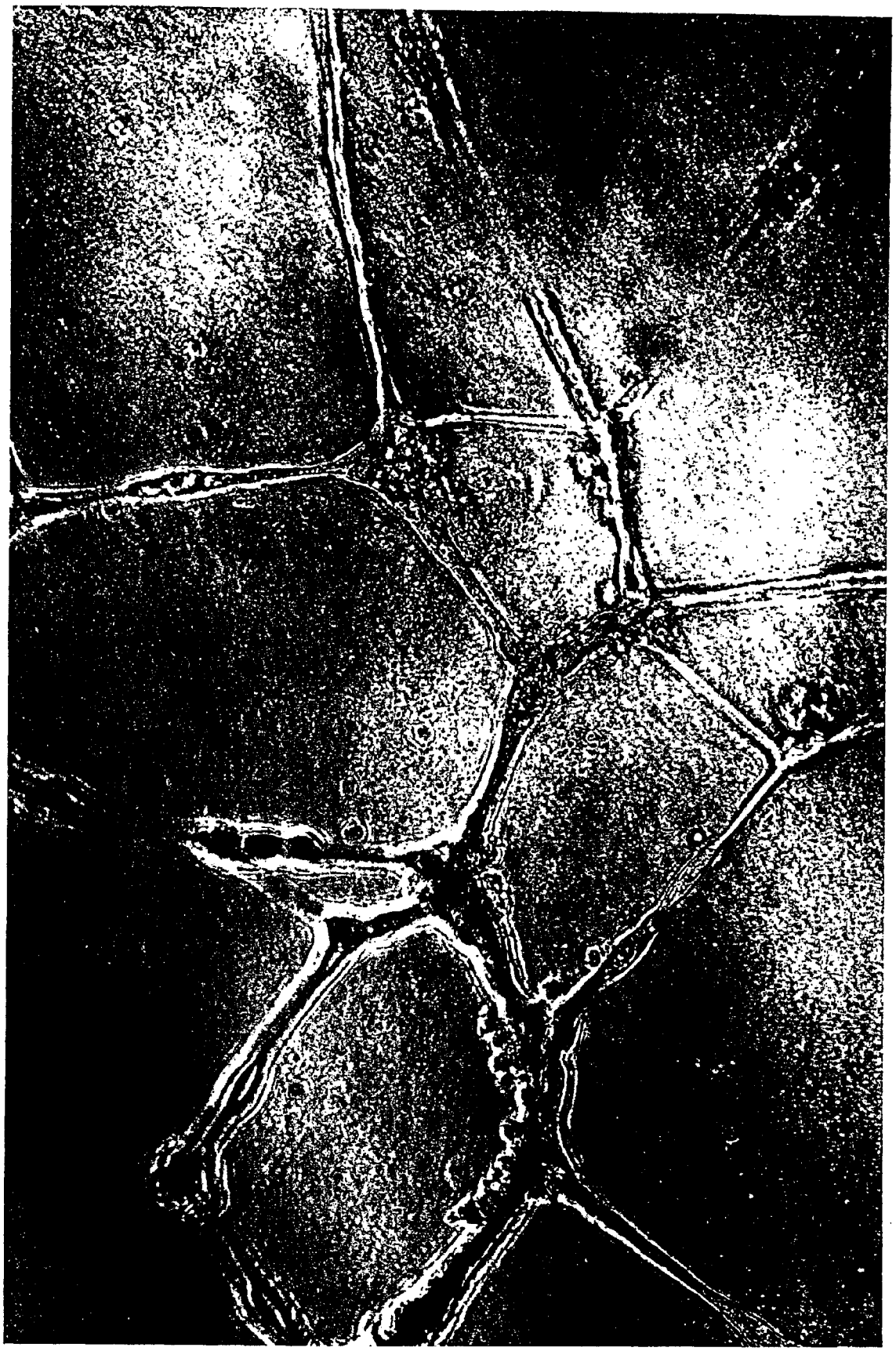

The concept of antiangiogenesis as a therapeutic approach for the treatment of cancer, particularly tumors, is being actively pursued as a promising strategy. The compound combretastatin A-4 has previously been demonstrated to disrupt the microtubules of human umbilical vein endothelial cells (HUVEC) in culture. Those studies confirmed that the tubulin-binding properties shown in cell-free systems are retained when the compound enters cells, and that tubulin binding is a significant component of the biological activity.

Thus, an object of the present invention is to provide new compounds that may be useful as tubulin binding agents.

A further object of the invention is to provide compounds that possess antiangiogenesis properties.

Yet another object of the invention is to provide compounds for use as therapeutic agents for the treatment of mammals, including humans, afflicted with cancer, particularly tumors.

Still a further object of the invention is to provide compounds for use as antimicrobials.

Results and Discussion

Preparation of the stilbenes of the present invention was accomplished as described in detail herein. The reaction sequence was initiated by protection of isovanillin as the tert-butyldiphenylsilyl ether 4. Benzaldehyde 4 was reduced using sodium borohydride to benzyl alcohol 5, followed by conversion to phosphonium bromide 6. Condensation of Wittig intermediate 6 with the respective halo-aldehyde using n-butyllithium in THF led to silyl group protected stilbenes 7-10. Subsequent deprotection (Scheme 2) with tetrabutylammonium fluoride afforded 3-halo-stilbenes 11-14. The Z isomers 11a, 13a and 14a were phosphorylated using dibenzylphosphite, diisopropylethyl-amine, N,N-dimethylaminopyridine and carbon tetrachloride in acetonitrile to provide bisbenzyl phosphates 15-17. Debenzylation of phosphate esters 15-17 was achieved using trimethylsilybromide followed by the corresponding base to produce phosphates 18-20. (See Pettit, G. R., et al., Antineoplastic Agents 440. Asymmetric Synthesis and Evaluation of the Combretastatin A-1 SAR Probes (1S,2S) and (1R,2R)-1-2-Dihydroxy-1-(2', 3'-dihydroxy-4'-methoxyphenyl)-2-(3",4",5"-trimethoxyphenyl)-ethane, J. Nat. Prod. 2000, 63, 969-974; Pettit, G. R., et al., Antineoplastic Agents 460. Synthesis of Combretastatin A-2 Prodrugs, Anticancer Drug Design 2001, 16, 185-194; Pettit, G. R., et al. Antineoplastic Agents 463. Synthesis of Combretastatin A-3 Diphosphates, Anticancer Drug Design 2000, 15, 397-404.; Ladd, D. L., et al.; A New Synthesis of 3-Fluoroveratrole and Z-Fluoro-3,4 Dimethoxy Benzaldahyde, Synth. Commun. 1985, 15, 61.)

Compared to the related combretastatins, the new halostilbenes or halocombstatins shown in Table I as compounds 11a through 20a, all exhibited very strong inhibition of cancer cell growth. The three stilbenes (11a, 13a, 14a) converted to phosphate salts all retained strong activity and demonstrated markedly better aqueous solubility than their 3-halo-stilbene precursors. The E geometrical isomers evaluated appeared in vitro to be much less effective as inhibitors of cancer cell growth.

Because of their potent cytotoxicity, the four halocombstatins (11a, 12a, 13a, and 14a) were compared to combretastatin A-4 (1a) for inhibitory effects on tubulin polymerization and on the binding of [³H]colchicine to tubulin. The results of this comparison are shown in Table II. These experiments demonstrate that the five compounds are essentially identical in their apparent interactions with tubulin. The four halocombretastatins inhibited the polymerization reaction with $IC_{50}$ values of 1.5-1.6 µM:M, versus an $IC_{50}$ value of 1.8 µM:M for CA4 (1a). The minor differences between the compounds were within experimental error as indicated by the standard deviations.

Similarly, all four cis-stilbenes were highly potent inhibitors of the colchicine binding assay. When present at a concentration one fifth of that of [$^3$H]colchicine but equimolar to the tubulin concentration, binding of the radio labeled ligand was inhibited by 75-89% (note that the lowest and highest inhibitory effects were observed with stilbenes 11a and 13a, which were the two compounds that displayed the greatest inhibitory effects in the polymerization assay). In an earlier study, combretastatin A-3 (3a), with a hydroxyl substituent instead of the methoxy group or a halogen at position C-3 in the A ring, was found to be about half as active as CA4 (1a) as an inhibitor of tubulin assembly, about one fifth as active as an inhibitor of colchicine binding to tubulin, and about one seventh as active as an inhibitor of cell growth. (See Lin, C. M., et al., Interactions of Tubulin with Potent Natural and Synthetic Analogs of the Antimitotic Agent Combretastatin: A Structure-activity Study, *Mol. Pharmacol.*, 1988, 34, 200-208). A related finding is that elimination of the C-3 substituent entirely, by replacing it with a hydrogen atom, results in about a 7-fold reduction in inhibitory effect on polymerization and complete loss of cytotoxic activity. (See Cushman, M., et al., Synthesis and Evaluation of (Z)-1-(4-methoxyphenyl)-2-(3,4,5-trimethoxyphenyl)ethane as Potential Cytotoxic and Antimitotic Agents, *J. Med. Chem.* 1992, 35, 2293-2306.)

Thus, while not intending to be bound by this theory, it appears the optimal activity observed with CA4 (1a) and the novel halocombstatins of the present invention requires a C-3 substituent of some size, where the fluorine atom may represent a minimum, Therefore, it seems unlikely that the predominant effect of the substituent results from direct enhancement of the interaction of ligand with protein. The A-ring substituents most likely cause the active cis-stilbenes to assume with greater probability a conformation that favors the drug-tubulin interaction. (See Hamel, E.; Evaluation of Antimitotic Agents by Quantitative Comparisons of Their Effects on the Polymerization of Purified Tubulin, *Cell Biochem. Biophys.*, In Press.)

Tubulin polymerization was evaluated by turbidimetry at 350 nm using Beckman DU7400/7500 spectrophotometers as described in detail elsewhere. (See National Committee for Clinical Laboratory Standards. Reference Method for Broth Dilution Antifungal Susceptibility Testing of Yeasts. Approved Standard M27-A. Wayne, Pa.: NCCLS, 1997.) Varying concentrations of drug were preincubated with 10 µM:M (10 mg/mL) purified tubulin (See Hamel, E., et al., Separation of Active Tubulin and Microtubule-associated Proteins by Ultracentrifugation and Isolation of a Component Causing the Formation of Microtubule Bundles, *Biochemistry* 1984, 23, 4173-4184). Samples were chilled on ice, GTP (0.4 mM) was added, and polymerization was followed at 30° C. The parameter measured was extent of the reaction after 20 minutes. Colchicine binding was measured as described in detail previously. Reaction mixtures contained 1.0 µM:M tubulin, 5.0:M [$^3$H]colchicine (from Dupont), and inhibitor at 1.0 µM:M. Incubation was for 10 minutes at 37° C.

The inventors have also demonstrated the ability of halocombstatins 11a and 12a to disrupt microtubules in human umbilical vein endothelial cells (HUVEC). HUVECs were isolated according to methods know to one of skill in the art (see Jaffe, E. A. et al., Culture of Human Endothelial Cells Derived From Umbilical Veins. Identification by Morphologic and Immunologic Criteria, *J. Clin Invest.* 1973, 52, 2754-2756.)

In a further detailed series of experiments, compound 11a (flurocombstatin) was further evaluated against HUVECs in vitro. These cells showed significant sensitivity to the fluorocombstatin (11a): $ED_{50}$ 0.00025 µg/mL. Cords length as well as junction numbers were markedly reduced at both 0.01 and 0.001 µg/mL compared to untreated controls. Such activity against endothelial cells is significant, as endothelial cells are known to play a central role in the angiogenic process.

The halocombstatins of the present invention appear to also have antimicrobial properties. More specifically, they appear to have antifungal and/or antibacterial properties. Antimicrobial evaluation of the halocombstatins involved susceptibility testing performed by the reference broth microdilution assay. The antimicrobial activities of the halocombstatins were very similar, targeting Gram-positive bacteria and the pathogenic fungi *Cryptococcus neoformans*, and results are shown in Table III. The sodium phosphate derivative (16a) of fluorocombstatin (11a) did not retain significant antimicrobial activity.

Similarly, the inventors have previously shown that combretastatin A-3 but not its sodium phosphate prodrug inhibited growth of the pathogenic fungus *Cryptococcus neoformans*. (See Pettit, G. R., et al., Antineoplastic Agents 463. Synthesis of Combretastatin A-3 Diphosphates, *Anticancer Drug Design* 2000, 15, 397-404.) To determine the antimicrobial activity of the present compounds, susceptibility testing was performed by the reference broth microdilution assay. (See National Committee for Clinical Laboratory Standards. Methods for Dilution Antimicrobial Susceptibility Tests for Bacteria that Grow Aerobically. Approved Standard M7-A5. Wayne, Pa.: NCCLS, 2000. National Committee for Clinical Laboratory Standards. Reference Method for Broth Dilution Antifungal Susceptibility Testing of Yeasts. Approved Standard M27-A. Wayne, Pa.: NCCLS, 1997.) The antimicrobial activities of the halocombretastatins of the present invention were very similar, targeting Gram-positive bacteria and *Cryptococcus neoformans*. This is illustrated in further detail in Table III. Thus, several of the novel compounds of the present invention appear to have potential as antimicrobial agents, such as antifungals and antibacterials.

EXPERIMENTAL SECTION

Materials and, Methods. All solvents (ether refers to diethyl ether) and reagents were obtained from commercial sources (Acros Organics, Sigma-Aldrich Co., Alfa Aesar, City Chemicals or Lancaster Synthesis, Inc.). The 3-iodo-4,5-dimethoxybenzaldehyde was purchased from Lancaster Synthesis, Solvents were redistilled. Solvent extracts of aqueous solutions were dried over anhydrous magnesium sulfate.

Gravity column chromatography was performed using silica gel from VWR Scientific 70-230 mesh) or from Merck (230-400 mesh). Analtech silica gel GHLF plates were employed for TLC.

All melting points were determined with an electrochemical digital melting point apparatus, Model 9100 or IA-9200, and are uncorrected. NMR spectra were recorded employing Varian Gemini 300 or Varian Unity 400 instruments. Chemical shifts are reported in ppm downfield from tramethylsilane as an internal standard in $CDCl_3$ or where noted in $D_2O$. High resolution mass spectra were obtained with a Kratos Ms-50 instrument (Midwest Center for Mass Spectroscopy, University of Nebraska-Lincoln) or in the Cancer Research Institute at Arizona State University with a Jeol LCmate instrument. Elemental analyses were determined by Galbraith Laboratories, Inc., Knoxville, Tenn.

General Procedure for Synthesis of Dimethoxyhalobenzaldehydes

3-Fluoro-4,5-dimethoxybenzaldehyde. To a stirred solution prepared from 100 mL of DMF and 5-fluorovanillin (lit 1.0 g, 5.88 mmol). After 15 minutes, iodomethane was added, and stirring at room temperature continued for 16 hours. The reaction was terminated by the addition of water, the mixture was extracted with hexane (3×100 ML), and solvents were removed in vacuo. Purification by flash chromatography on a column of silica gel using hexane-ethyl acetate (4:1) as eluent afforded a colorless solid (1 g, 93% yield); mp 51-53° C. (Lit[17] mp 52-53° C.) $^1$H-NMR (300 MHz, $CDCl_3$) δ 3.94 (s, 3H), 4.05 (s, 3H), 7.24 (s, 1H), 7.26 (s, 1H), 9.82 (s, 1H).

3-Chloro-4,5-dimethoxybenzaldehyde. The preceding reaction was repeated with 5-chlorovanillin (10 g, 54 mmol) to give this compound, which was isolated as set forth in the preceding experiment to afford a colorless solid (10.4 g, 97% yield); mp 88-90° C. (Lit[17] mp 87-89° C.); $^1$H-NMR (300 MHz, $CDCl_3$) δ 3.95 (s, 3H), 3.96 (s, 3H), 7.36 (d, J=1.5 Hz, 1H), 7.50 (d, J=1.5 Hz, 1H), 9.85 (s, 1H).

3-Bromo-4,5-dimethoxybenzaldehyde. The experiment was repeated with 5-bromovanillin (10 g, 43-3 mmol) as described for the preceding aldehydes to give compound (6) which was separated by flash chromatography on a column of silica gel using hexane-ethyl acetate (9:1) as eluent to afford a colorless solid (8 g, 75% yield); mp 64-65° C.; $^1$H-NMR (300 MHz, $CDCl_3$) δ 3.94 (s, 3H), 3.95 (s, 3H), 7.40 (d, 1H, J=1.8 Hz), 7.65 (d, 1H, J=1.8 Hz), 9.85 (s, 1H).

3,5-diiodo-4-methoxybenzaldehyde

3-Iodo-4,5-dimethoxybenzaldehyde was obtained from Sigma-Aldrich Chemical Company.

3-O-tert-Butlydiphenylsiloxy-4-methoxybenzyltriphenylphosphonium bromide (6). To 400 mL of dry dichloromethane was added benzyl alcohol 5 (84 g, 214 mmol) (Pettit, G. et al., Antineoplastic Agents 463, Synthesis of Combretastatin A-3 Diphosphates. Anticancer Drug Design 2000, 15, 397-404) and phosphorous tribromide (10 mL, 106 mmol, 0.5 eq). The reaction mixture was allowed to stir for 16 hours, and was terminated by the addition of 10% $NaHCO_3$, and the product was extracted with dichloromethane. The solvent was removed (in vacuo), the resulting benzyl bromide was dissolved in 500 mL of toluene, and triphenylphosphine (62 g, 236 mmol, 1.1 eq) was added. The mixture was heated at reflux for 1 hour and stirred at RT for 15 hours. The precipitate was collected and triturated with ether to afford 132 g of phosphonium salt, in 86% yield; $^1$H-NMR (300 MHz $CD_3OD$) δ 1.00 (s, 9H), 3.51 (s, 3H), 4.69 (d, 2H, J=17.4 Hz), 6.34 (dt, 1H, J=2.4, 8.1 Hz), 6.59 34 (d, 1H, J=8.1 Hz), 6.65 34 (t, 1H, J=2.4 Hz); and $^{13}$C NMR (75 MHz $CD_3OD$) δ 20.47, 27.07, 55.60, 102.20, 113.15, 118.48, 119.60, 123.43, 126.56, 126.85, 128.17, 128.74, 131.07, 131.12, 133.91, 135.10, 135.23, 136.17, 136.55, 146.55, 152.76.

General Procedure for the Stilbene Syntheses

3-Fluoro-4,4',5-trimethoxy-3'-O-tert-butyldiphenylsilyl-Z-stilbene (7a). To a mixture of phosphonium salt 6 (4.7 g, 6.5 mmol) and tetrahydrofuran (25 ml, cooled to −78° C.) was added n-BuLi (2.6 mL, 2.5 M, 6.5 mmol, over 5 minutes), followed by stirring for one hour. Next, 3-fluoro-4,5-dimethoxybenzaldehyde (1 g. 5.4 mmol) in tetrahydrofuran (10 ml) was added (dropwise) over 30 minutes. The mixture was allowed to warm to room temperature, and stirring continued for 16 hours. The reaction was terminated by the addition of water (50 mL), the product was extracted with ethyl acetate, solvents were removed in vacuo, and the residue (1:1 E/Z, 75% yield) obtained was subjected to flash chromatography on silica gel using hexane-ethyl acetate (9:1) as eluent to afford Z-stilbene 7a (1 g, 34%) as a clear oil; $^1$H-NMR (300 MHz, $CDCl_3$) δ 1.07 (s, 9H), 3.46 (s, 3H), 3.65 (s, 3H), 3.90 (s, 3H), 6.24 (d, 1H, J=12 Hz), 6.33 (d, 1H, J=12 Hz), 6.56 (m, 2H), 6.72 (m, 3H), 7.35 (m, 6H), 7.70 (m, 4H); and $^{13}$C NMR (75 MHz, $CDCl_3$) δ 19.75, 26.65, 55.07, 55.99, 61.43, 108.26, 108.28, 109.40, 109.55, 111.74, 120.83, 122.42, 127.36, 127.46, 127.48, 127.70, 129.37, 129.50, 129.63, 130.32, 132.59, 132.66, 133.57, 134.77, 135.27, 135.83, 135.95, 144.74, 149.88, 152.91, 152.95, 154.59, 156.53; HRMS (calcd for $C_{33}H_{36}FO_4Si$) [M+H]$^+$ 543.2368, found 543.2372.

Further elution gave the E-isomer 7b (1.2 g, 41% yield): $^1$H-NMR (300 MHz, $CDCl_3$) δ 1.19 (s, 9H), 3.58 (s, 3H), 3.92 (s, 3H, 3.95 (s, 3H), 6.48 (d, 1H, J=15.9 Hz), 6.76 (d, 1H, J=8.7 Hz), 6.77 (d, 1H, J=16.5 Hz), 6.8 (d, 1H, J=1.5 Hz), 6.92 (d, 1H, J=2.1 Hz), 6.97 (dd, 1H, J=1.8, 8.4 Hz), 7.42 (m, 6H), 7.78 (m, 4H). $^{13}$C NMR (75 MHz, $CDCl_3$) δ 19.76, 26.62, 55.20, 56.13, 61.39, 105.40, 106.45, 106.75 112.62, 117.62, 120.57, 125.26, 127.48, 128.52, 129.58, 139.68, 133.15, 133.28, 133.59, 135.35, 145.14, 150.52, 153.52. HRMS calcd for. $C_{33}H_{36}FO_4Si$ [M+H]$^+$ 543.2368, found 543.2392.

3-Chloro-4,4',5-trimethoxy-3'-O-tert-butyl-diphenylsilyl-Z-stilbene (8a). The experimental procedure noted above for 7a was repeated with 3-Chloro-4,5-dimethoxybenzaldehyde (2.8 g, 14 mmol) to yield the Z-isomer 8a (1.6 g, 21%) as a clear oil: $^1$H-NMR (300 MHz, $CDCl_3$) δ 1.07 (s, 9H), 3.46 (s, 3H), 3.60 (s, 3H), 3.84 (s, 3H), 6.24 (d, 1H, J=12 Hz), 6.34 (d, 1H, J=12 Hz), 6.59 (s, 1H, J=7.5 Hz), 6.66 (s, 1H), 6.73 (s, 1H), 6.73 (d, 1H, J=9 Hz) 6.81 (s, 1H), 7.33 (m, 6H), 7.65 (dd, 4H, J=6.67, 1.2 Hz), and $^{13}$C NMR (125 MHz, $CDCl_3$) δ 19.76, 26.66, 55.11, 55.82, 60.71, 111.35, 111.75, 120.86, 122.40, 122.46, 127.13, 127.38, 127.85, 129.32, 129.51, 130.27, 133.60, 133.81, 135.27, 144.22, 144.75, 149.91, 153.12; HRMS calcd for. $C_{33}H_{36}ClO_4SiCl$ 561.2042 [M+H]$^+$, found 561.2449, Cl, 559.2071. [M+H]$^+$; found 559.1996.

Continued elution of the chromatographic column led to the isolation of E-stilbene 8b (4.9 g, 62% yield) as a clear oil; $^1$H-NMR (300 MHz, CDCl$_3$) δ 1.14 (s, 9H), 3.56 (s, 3H), 3.86 (s, 3H), 3.90 (s, 3H), 6.44 (d, 1H, J=16.5 Hz), 6.74 (d, 1H, J=16.5 Hz), 6.74 (s, 1H), 6.82 (d, 1H, J=1.5 Hz), 6.87 (d, 1H, J=1.8 Hz), 6.94 (dd, 1H, J=8.1, 2.1 Hz), 6.99 (d, 1H, J=1.5 Hz), 7.40 (m, 6H), 7.75 (M, 4H); and $^{13}$C NMR (75 MHz, CDCl$_3$) δ 19.82, 26.67, 55.30, 55.09, 60.78, 108.43, 112.13, 117.71, 119.78, 120.59, 124.97, 127.53, 128.78, 129.61, 129.73, 133.65, 134.31, 135.41, 144.55, 150.61, 153.74.

3-Bromo-4,4',5-trimethoxy-3'-O-tert-butyl-diphenylsilyl-Z-stilbene (9a). To 100 mL of THF was added phosphonium salt 6 (25.7 g, 36 mmol) and the solution cooled to −78° C. Once the temperature reached −78° C., n-BuLi (14.4 mL, 2.5 M, 36 mmol) was added over 5 minutes followed by stirring for one hour. Then the bromo-benzaldehyde (8 g, 33 mmol, in 100 mL THF) was added dropwise over 30 minutes. The mixture was allowed to warm to room temperature and stirring continued for 16 hours. The reaction was then terminated by the addition of water (50 mL), product was extracted with ethyl acetate, solvents were removed in vacuo, and the residue was separated by column chromatography to yield 4.2 g 9a (Z-stilbene), 2:1, E:Z (65% overall yield); HRMS (M+Na)+ 625.1364, (M+Na)+2 627.1338; IR 2962, 1730, 1510, 1267, 908, 735, 650 cm$^{-1}$; $^1$H NMR (300 MHz, CDCl$_3$) δ 1.07 (s, 9H), 3.45 (s, 3H), 3.58 (s, 3H), 3.82 (s, 3H), 6.97 (d, 1H, J=1.5 Hz), 6.23 (d, 1H, J=12 Hz), 6.32 (d, 1H, J=12 Hz), 6.52 (d, 1H, J=8.1 Hz), 6.71 (dd, 1H, J=1.5 Hz, J=8.1 Hz), 7.57 (d, 1H, J=1.5 Hz), 7.32 (m, 6H), 7.65 (dd, 4H); $^{13}$C NMR (100 MHz, CDCl$_3$) δ 152.87, 149.79, 145.16, 144.66, 135.17, 134.37, 133.52, 130.40, 129.43, 129.24, 127.30, 126.90, 125.16, 122.40, 120.79, 117.18, 112.01, 111.71, 94.38, 60.61, 55.81, 55.15, 21.10.

Further elution of the chromatogram led to isolation of 8.1 g of the E-isomer 9b: IR 2934, 2859, 1710, 1510, 1275, 908, 732, 650 cm$^{-1}$; $^1$H-NMR (300 MHz, CDCl$_3$) δ 1.14 (s, 9H), 3.54 (s, 3H), 3.84 (s, 3H), 3.88 (s, 3H),), 6.46 (d, 1H, J=12 Hz), 6.76 (d, 1H, J=12 Hz), 6.71 (d, 1H, J=8.1 Hz), 6.85 (d, 1H, J=2.1 Hz), 6.87 (d; 1H, J=2.1), 6.94 (dd, 1H, J=8.4 Hz, J=2.4 Hz), 7.15 (d, 1H, J=2.4) 7.38 (m, 6H), 7.74 (dd, 4H); and $^{13}$C-NMR (75 MHz, CDCl$_3$) δ 19.76, 26.65, 55.25, 56.03, 60.59, 109.18, 109.85, 112.13, 117.70, 120.57, 122.59, 124.79, 127.48, 128.80, 129.58, 133.64, 134.91, 135.35, 145.16, 150.57, 153.58.

3-Iodo-4,4',5-trimethoxy-3'O-tert-butyl-diphenyl-Z-stilbene (10a). A gradient column chromatogram from 0-3% ethyl acetate in hexane afforded Z-stilbene 10a (1.4 g) in 21% yield mp 122-124° C.: HRMS, found: [+H]$^+$ 651.1474. $C_{33}H_{36}O_4Si$ requires [M+H]$^+$ 651.1427; $^1$H-NMR (300 MHz, CDCl$_3$) δ 1.07 (s, 9H), 3.45 (s, 3H), 3.55 (s, 3H), 3.79 (s, 3H), 6.21 (d, 1H, J=12 Hz), 6.31 (d, 1H, J=12 Hz), 6.59 (d, 1H, J=7.8 Hz), 6.72 (s, 2H), 6.77 (dd, 1H, J=7.8, 1.5 Hz), 7.19 (d, 1H, J=1.8 Hz), 7.32 (m, 6H), 7.64 (d, 4H, J=7.5 Hz), and $^{13}$C NMR (75 MHz, CDCl$_3$) δ 19.68, 26.62, 55.05, 55.56, 60.33, 91.94, 111.72, 113.09, 120.78, 122.43, 126.73, 127.33, 129.32, 130.28, 130.93, 133.54, 135.17, 144.70, 149.82, 151.82.

General Procedure for Cleavage of the Silyl Ether Protecting Group

3-Fluoro-4,4',5-trimethoxy-3'-hydroxy-Z-stilbene(11a, Fluorcombstatin). A solution prepared from Z-isomer 7a (2.4 g, 4.4 mmol), tetrahydrofuran (50 ml) and 1M tetrabutylammonium fluoride (4.5 ml, 4.5 mmol) was stirred from 3 hours. The reaction was terminated by the addition of water (5 ml), the mixture was extracted with ethyl acetate and the solvents were removed in vacuo. Separation by flash chromatography using: 1:4 ethyl acetate-hexane as eluent provided Z-stilbene (11a) (1.12 g, 83%) as a colorless solid, which was recrystallized from ethyl acetate-hexane: mp 93-94° C.; (300 MHz, CDCl$_3$) δ 3.67 (s, 3H), 3.87 (s, 3H), 3.90 (s, 3H), 5.30 (bs, 1H), 6.35 (d, J=12 Hz, 1H), 6.48 (d, J=12 Hz, 1H), 6.61 (d, J=2.4 Hz, 1H), 6.64 (d, J=1.8 Hz, 1H), 6.72 (d, J=8.4 Hz, 1H), 6.75 (dd, J=1.5, 8.4 Hz, 2H), 6.86 (d, J=1.5 Hz, 1H); $^{13}$C NMR (75 MHz, CDCl$_3$) δ 55.87, 56.01, 61.39, 108.24, 109.37, 109.57, 110.32, 114.83, 120.88, 127.72, 130.03, 130.14, 132.38, 132.48, 135.81, 135.95, 145.15, 145.78, 152.85, 152.88, 154.22, 156.65; and $^{19}$F NMR (CDCl$_3$) δ−11.32 (d, J=12.8 Hz, 1H). HRMS calcd for $C_{17}H_{18}FO_4$ 305.1189 [M+H]$^+$.

3-Fluoro-4,4',5-trimethoxy-3'-hydroxy-E-stilbene (11b). Cleavage of silyl ester 7b (150 mg, 0.27 mmol) was performed as described for the synthesis of 11a. Separation by flash chromatography on silica using ethyl acetate-hexane (3:7) afforded a colorless solid 11b (75 mg, 880% yield): mp 86-87° C., $^1$H NMR (300 MHz, CDCl$_3$) δ 3.87 (s, 3H), 3.90 (s, 3H), 3.93 (s, 3H), 5.75 (bs, 1H), 677-6.86 (m, 5H), 6.93 (m, 1H), 6.86 (d, J=1.8 Hz, 1H). $^{13}$C NMR (75 MHz, CDCl$_3$) δ 55.87, 56.18, 61.39, 100.64, 105.68, 106.51, 106.79, 107.55, 110.63, 111.76, 119.30, 125.80, 127.61, 128.62, 129.53, 130.56, 133.13, 133.23, 134.73, 136.41, 145.78, 146.59, 153.57, 154.40, 157.64.

3-Chloro-4,4',5-trimethoxy-3'-hydroxy-Z-stilbene (12a). Deprotection of silyl ester 8a (1.5 g, 2.7 mmol) was conducted as summarized for the synthesis of 11a. Separation by flash chromatography on silica using ethyl acetate-hexane (3:7) gave compound 12a (754 mg, 89%0). Recrystallization from hexane gave a white solid; mp 105-106° C.; $^1$H-NMR (300 MHz, CDCl$_3$) δ 3.65 (s, 3H), 3.86 (s, 3H), 3.88 (s, 3H), 5.52 (s, 1H), 6.36 (d, 1H, J=12.3 Hz), 6.49 (d, 1H, J=12 Hz), 6.75 (m, 3H), 6.88 (m, 2H); $^{13}$C NMR (75 MHz, CDCl$_3$) δ 55.86, 55.94, 60.76, 110.37, 111.40, 114.86, 114.94, 121.05, 122.51, 127.60, 127.92, 130.15, 130.43, 133.74, 144.36, 145.31, 145.92, 153.21.

3-Chloro-4,4',5-trimethoxy-3'-hydroxy-E-stilbene (12b). Column chromatography (elution with 7:3 hexane-ethyl acetate) afforded a colorless solid, E-isomer 12b, mp 138-140° C., in 79% yield: $^1$H-NMR (300 MHz, CDCl$_3$) δ 3.87 (s, 3H), 3.88 (s, 3H), 3.90 (s, 3H), 5.69 (bs, 1H), 6.79 (d, 1H, J=15.9 Hz), 6.81 (d, 1H, J=8.4 Hz), 6.90 (d, 1H, J=1.5 Hz), 6.90 (d, 1H, J=15.9 Hz), 6.94 (dd, 1H, J=8.1, 1.5 Hz), 7.08 (dd, 1H, J=1.8 Hz), 7.11 (d, 1H, J=2.1 Hz); $^{13}$C NMR (75 MHz, CDCl$_3$) δ 55.93, 56.06, 60.74, 100.66, 108.66, 110.65, 111.77, 119.38, 119.79, 125.49, 128.41, 128.85, 130.59, 134.24, 144.65, 145.79, 146.61, 153.78. HRMS calcd for $C_{17}H_{17}ClO_4$ 321.0894 [M+H]$^+$, found 321.0893. Anal. Calcd for $C_{17}H_{17}ClO_4$ C, H.

3-Bromo-4',5-trimethoxy-3'-hydroxy-Z-stilbene (13a). The silyl ester cleavage reaction for 9a (4 g, 6.6 mmol) was completed as described for the synthesis of phenol 11a. Isolation by flash chromatography on silica gel using ethyl acetate-hexane (1:4) gave compound 13a (2.22 g of 92%). Recrystallization from hexane afforded a colorless solid: mp 108-109° C.; HRMS calcd for $C_{17}H_{17}BrO_4$ 364.0303, found [M$^{+2}$] 366.0287; $^1$H NMR (300 MHz, CDCl$_3$) δ 3.63 (s, 3H) 3.84 (s, 3H), 3.86 (s, 3H), 6.34 (d, 1H, J=12 Hz), 6.49 (d, 1H, J=12 Hz), 6.73 (d, 1H, J=8.4 Hz), 6.77 (dd, 1H, J=8.7, 1.8 Hz), 6.79 (d, 1H, J=1.8 Hz), 6.86 (d, 1H, J=1.5 Hz), 7.04 (d, 1H, J=1.5 Hz). $^{13}$C NMR (75 MHz, CDCl$_3$) δ 55.77, 55.88, 60.56, 110.45, 112.13, 114.98, 117.18, 121.01, 125.28, 127.33, 130.07, 130.43, 134.37, 145.32, 146.02, 153.03. IR 3539, 3441, 3011, 2939, 2839, 1554, 1510, 1273, 1047, 908, 732 cm$^{-1}$. HRMS calcd for $C_{17}H_{17}O_4{}^{81}Br$. 366.0287.

3-Bromo-4',5-trimethoxy-3'-hydroxy-E-stilbene (13b). By the same procedure used to obtain phenol 13a, silyl ester 9b was converted to E phenol 13b, and isolated by flash chromatography on silica gel with ethyl acetate-hexane (3:7) to give E-isomer 13b (0.14 g, 81%). Recrystallization from hexane gave colorless solid. mp 152-154° C.; $^1$H NMR (300 MHz, CDCl$_3$) δ 3.86 (s, 3H), 3.89 (s, 3H), 3.90 (s, 3H), 6.80 (d, 1H, J=15.9 Hz), 7.38 (d, 1H, J=15.9 Hz), 6.82 (d, 1H, J=8.4 Hz), 6.96 (dd, 1H, J=8.4, 2.4 Hz), 6.88 (s, 1H), 7.11 (d, 1H, J=1.8 Hz), 7.25 (d, 1H, J=1.5 Hz); and $^{13}$C NMR (75 M1 Hz, CDCl$_3$) δ 56.00, 56.11, 60.58, 94.36, 109.32, 110.60, 11.72, 117.81, 119.32, 122.58, 125.29, 128.82, 130.53, 134.81, 145.60, 145.70, 146.50, 153.53.

3-Iodo-4',5-trimethoxy-3'-hydroxy-Z-stilbene (14a). The silyl ester cleavage reaction for 10a was completed as described for the phenol 11a. The crude product was separated by column chromatography using 1:4 ethyl acetate-hexane as eluent to give 1.38 g of Z-isomer 14a in 81% yield: mp 92-94° C.: HRMS calc for $C_{17}H_{18}O_4Si$ found (M+H)$^+$ 413.0250. $^1$H NMR (300 MHz, CDCl$_3$) δ 3.61 (s, 3H), 3.81 (s, 3H), 3.84 (s, 3H), 6.32 (d, 1H, J=12 Hz), 6.34 (s, 1H), 6.56 (d, 1H, J=12 Hz), 6.75 (s, 1H), 6.83 (d, 1H, J=1.8 Hz), 6.85 (s, 3H), 7.25 (d, 1H, J=1.5 Hz); and $^{13}$C NMR (75 MHz, CDCl$_3$) δ 55.56, 55.82, 60.33, 91.78, 110.50, 113.11, 115.00, 120.91, 126.96, 129.94, 130.28, 135.93 145.29, 146.10, 147.67, 151.79. IR 3543, 3011, 2937, 2841, 1510, 1273, 1001, 908, 732 cm$^{-1}$.

3-Iodo-4',5-trimethoxy-3'-hydroxy-E-stilbene (14b). Separation by column chromatography (30% ethyl acetate-hexane as eluent) gave 0.29 g of E-isomer 14b in 98% yield: mp 111-1130° C.; $^1$H NMR (300 MHz, CDCl$_3$) δ 3.84 (s, 3H), 3.87 (s, 3H), 3.88 (s, 3H), 5.85 (bs, 1H), 6.77 (d, 1H, J=16.5 Hz), 6.89 (d, 1H, J=16.5 Hz), 6.82 (s, 1H), 6.96 (s, 1H), 6.93 (d, 1H, J=2.4 Hz), 7.11 (d, 1H, J=1.5 Hz), 7.46 (d, 1H, J=1.5 Hz); and $^{13}$C NMR (75 MHz, CDCl$_3$) δ 55.85, 60.41, 92.56, 110.40, 110.63, 111.77, 119.28, 124.97, 128.36, 128.70, 130.15, 135.71, 145.71, 146.56, 148.11, 152.44.

Dibenzyl (Z)-3-fluoro-4',5-trimethoxy-Z-stilbene 3'-O-phosphate (15). Z-stilbene 11a (1.1 g, 3.6 mmol) in 20 mL of acetonitrile (20 mL) and 3.5 mL (36 mmol) of carbon tetrachloride was cooled to −10° C., and stirred for 10 minutes. Then DIPEA (1.3 mL, 7.4 mmol), immediately followed by DMAP (44 mg, 0.36 mmol), were added. After 1 minute dibenzyl phosphite (1.2 mL, 5.4 mmol) was added over 5 minutes, and the mixture was stirred for an additional 3 hours at −10° C. The reaction was terminated by the addition of 0.5 M KH$_2$PO$_4$, the mixture was extracted with ethyl acetate, solvents were removed in vacuo, and the product was isolated by column chromatography (1:1 elution with ethyl acetate-hexane) to yield 1.5 g of phosphate in 74% yield: b.p. dec. 280° C. (0.01 mmHg); $^1$H-NMR (500 MHz, CDCl$_3$) δ 3.65 (s, 3H), 3.77 (s, 3H), 3.87 (s, 3H), 5.12 (s, 2H), 5.14 (s, 2H), 6.38 (d, 1H, J=12 Hz), 6.43 (d, 1H, J=12 Hz), 6.57 (s, 1H) 6.62 (dd, 1H, J=1.5, 11.5 Hz), 6.78 (d, 1H, J=8.5 Hz), 7.03 (d, 1H, J=8.5 Hz), 7.12 (s, 1H), 7.82 (m, 10H); $^{13}$C NMR (125 MHz, CDCl$_3$) δ; and $^{31}$P NMR (162 MHz CDCl$_3$) δ−7.84 (s).

Dibenzyl (3-bromo-4',5-trimethoxy-Z-stilbene 3'-O-phosphate (16). The preceding reaction (see Compound 15) was repeated with Z-stilbene 13a (1 g, 2.7 mmol) to afford 1.6 g of phosphate 16 in 94% yield: b.p. dec. 271° C. (0.01 mmHg); $^1$H-NMR (300 MHz, CDCl$_3$) δ 3.59 (s, 3H), 3.76 (s, 3H), 3.79 (s, 3H), 5.11 (s, 2H), 5.13 (s, 2H), 6.37 (d, 1H, J=12.4 Hz), 6.43 (d, 1H, J=12 Hz), 6.72 (d, 1H, J=1.5 Hz), 6.78 (d, 1H, J=8.4 Hz), 7.02 (d, 1H, J=8.2 Hz), 7.03 (d, 1H, J=2.4 Hz), 7.10 (d, 1H, J=1.8 Hz), 7.28 (m, 10H); $^{13}$C NMR (75 MHz, CDCl$_3$) δ 55.77, 55.88, 60.51, 65.59, 69.67, 69.73, 111.83, 112.22, 117.23, 121.96, 121.99, 125.04, 126.32, 126.75, 127.30, 127.69, 127.77, 127.88, 128.31, 128.35, 129.46, 129.47, 133.93, 135.44, 135.51, 139.30, 139.38, 145.30, 149.77, 149.82, 152.99; and $^{31}$P NMR (162 MHz CDCl$_3$) 5-7.84 (s).

Dibenzyl 3-iodo-4',5-trimethoxy-Z-stilbene 3'-O-phosphate (17). The phosphorylation reaction used to obtain phosphate 15 was repeated with Z-stilbene 14a (2.39 g, 0.95 mmol) to obtain 0.55 g of Z-stilbene 17 in 86% yield as a colorless oil. b.p. dec. 274° C. (0.01 mmHg); HRMS calc for $C_{31}H_{31}PO_7$ [M+H]$^+$ 673.0852; found [+H]$^+$, 673.0808. $^1$H-NMR (300 MHz, CDCl$_3$) δ 3.51 (s, 3H), 3.65 (s, 3H), 3.72 (s, 3H), 5.04 (s, 2H), 5.06 (s, 2H), 6.36 (d, 1H, J=9 Hz), 6.42 (d, 1H, =9 Hz), 6.77 (d, 1H, J=1.2 Hz), 6.89 (d, 1H, J=6 Hz), 7.02 (d, 1H, J=6 Hz), 7.01 (s, 1H), 7.19 (d, 1H, J=1.2 Hz), 7.28 (m, 10H); and $^{13}$C-NMR (75 MHz, CDCl$_3$) δ 56.20, 56.50, 60.73, 71.18, 71.24, 92.73, 113.72, 114.23, 122.58, 122.61, 128.10, 128.93, 129.50, 129.56, 130.18, 130.85, 130.86, 131.87, 136.26, 136.66, 136.73, 140.32, 140.3, 149.12, 151.21, 151.25, 153.26.

General Procedure for Synthesis of Phosphate Cation Derivatives

Method A. Each of the metal cation containing salts were obtained by the procedure outlined below for preparing sodium salt 19a. The metal counter ions were introduced by treatment of the phosphoric acid with either the corresponding hydroxide (e.g., potassium, lithium) or acetate (e.g. magnesium).

Sodium 3-bromo-4',-5-trimethoxy-Z-stilbene 3'-O-phosphate (19a). To a solution of dibenzyl phosphate 16 (0.28 g, 0.45 mmol) in dry dichloromethane (10 mL) was added trimethylsilylbromide (125 μL, 0.95 mmol). The reaction mixture was stirred for 30 minutes under argon, and the reaction was terminated by the addition of methanol (20 mL).

Following removal of solvents (in vacuo), the free phosphoric acid was dissolved in ethanol (10 mL) and sodium methoxide (49 mg, 0.9 mmol) were added to the residue. After the reaction mixture was stirred for 30 minutes, the precipitate was collected and washed with ether to provide sodium salt 19a (0.17 g) as a colorless solid: m.p. 196-197° C.; $^1$H—N (300 MHz, D$_2$O) δ 3.53 (s, 3H), 3.68 (s, 3H), 3.70 (s, 3H), 6.52 (d, 1H, J=12 Hz), 6.72 (d, 1H, J=12 Hz), 6.75 (s, 1H), 6.77 (s, 1H), 6.79 (s, 1H), 7.01 (s, 1H), 7.15 (s, 1H).

Sodium 3-fluoro-4,4',5-trimethoxy-Z-stilbene 3'-O-phosphate (18a). m.p. 200-202° C.; $^1$H-NMR, (300 MHz, D$_2$O) δ 3.52 (s, 3H), 3.67 (s, 3H), 3.68 (s, 3H), 6.52 (d, 1H, J=12 Hz), 6.71 (d, 1H, J=12 Hz), 6.72 (s, 1H), 6.78 (s, 1H), 6.79 (s, 1H), 7.03 (s, 1H), 7-16 (s, 1H).

Lithium 3-bromo-4,4',5-trimethoxy-Z-stilbene 3'-O-phosphate (19b). m.p. 265-268° C. (dec); $^1$H NMR (300 MHz, D$_2$O) δ 3.53 (s, 3H), 3.66 (s, 3H), 3.69 (s, 3H), 6.35 (d, 1H, J=12 Hz), 6.52 (d, 1H, J=12 Hz), 6.70 (s, 2H), 6.81 (d, 1H, J=1.5 Hz), 7.01 (d, 1H, J=1.5 Hz), 7.23 (s, 1H).

Potassium 3-bromo-4,4',5-trimethoxy-Z-stilbene 3'-O-phosphate (19c). m.p. 230-233° C. (dec); $^1$H-NMR (300 MHz, D$_2$O) δ 3.53 (s, 3H), 3.66 (s, 3H), 3.69 (s, 3H), 6.35 (d, 1H, J=12 Hz), 6.52 (d, 1H, J=12 Hz), 6.70 (s, 2H), 6.81 (d, 1H, J=1.5 Hz), 7.01 (d, 1H, J=1.5 Hz), 7.23 (s, 1H).

Cesium 3-bromo-4,4',5-trimethoxy-phenyl-Z-stilbene 3'-O-phosphate (19d). m.p. 233-235° C.; $^1$H-NMR (300 MHz, DMSO) δ 3.51 (s, 3H), 3.62 (s, 3H), 3.65 (s, 3H), 6.38 (d, 1H, J=12. Hz), 6.50 (d, 1H, J=12 Hz), 6.71 (s, 1H), 6.83 (d, 1H, J=1.5 Hz), 7.03 (d, 2H, J=1.5 Hz), 7.23 (s, 1H).

Rubidium 3-bromo-4,4',5-trimethoxy-Z-stilbene 3'-O-phosphate (19e). m.p. 204-206° C.; $^1$H-NMR (300 MHz, DMSO) δ 3.50 (s, 3H), 3.64 (s, 3H), 3.66 (s, 3H), 6.35 (d, 1H, J=12 Hz), 6.52 (d, 1H, J=12 Hz), 6.68 (s, 2H), 6.80 (d, 2H, J=1.5 Hz), 7.00 (d, 2H, J=1.5 Hz), 7.25 (s, 1H).

Calcium 3-bromo-4,4',5-trimethoxy-Z-stilbene 3'-O-phosphate (19f). m.p. 245-248° C. (dec); $^1$H-NMR (300 MHz, DMSO) δ 3.53 (s, 3H), 3.69 (s, 3H), 3.70 (s, 3H), 6.33 (d, 1H, J=12 Hz), 6.50 (d, 1H, J=12 Hz), 6.71 (s, 2H), 6.81 (d, 2H, J=1.5 Hz), 7.99 (d, 2H, J=1.5 Hz), 7.23 (s, 1H).

Magnesium 3-bromo-4,4',5-trimethoxy-Z-stilbene 3'-O-phosphate (19 g). m.p. 290-285° C. (dec); $^1$H-NMR (300 MHz, DMSO) δ 3.50 (s, 3H) 3.60 (s, 3H), 3.65 (s, 3H), 6.33 (d, 1H, J=12 Hz), 6.50 (d, 1H, J=12 Hz), 6.68 (s, 2H), 6.79 (d, 2H, J=1.5 Hz), 7.00 (d, 2H, J=1.5 Hz), 7.21 (s, 1H).

Sodium 3-iodo-4,4,5-trimethoxy-Z-stilbene 3'-O-phosphate (20a). m.p. 194-195° C., $^1$H-NMR (300 MHz, D$_2$O) δ 3.50 (s, 3H), 3.67 (s, 3H), 3.68 (s, 3H), 6.50 (d, 1H, J=12 Hz), 6.70 (d, 1H, J=12 Hz), 6.72 (s, 1H), 6.77 (s, 1H), 6.79 (s, 1H), 7.01 (s, 1H), 7.13 (s, 1H).

Method B The potassium salt 18c (approximately 30 mg) was dissolved in de-ionized water (1 mL) and applied to a Dowex-50w (HCR-W2) resin column (amine or amino acid) and developed by water. The eluent was concentrated by freeze drying to give the required compound.

3-Iodo-4,4',5-trimethoxy-3-O-tert-butyldiphenylsilyl-z-stilbene (10a) and 3-Iodo-4,4',5-trimethoxy-3'-O-tert-butyldiphenylsilyl-E-stilbene (10b)

Method A. Phosphonium bromide 6 (3.67 g, 5.13 mmol) was dissolved in DCM at 0° C. Sodium hydride (60% dispersion in mineral oil, 0.41 g, 10.2 mmol) was added and the mixture turned orange. Next, 3-iodo-4,5-dimethoxybenzaldehyde (1 g, 3.42 mmol) was added and stirring was continued for 21 hrs. The reaction was terminated by adding water (50 mL) and extracted with DCM (3×50 mL), which was dried, filtered and concentrated. The oil obtained was subjected to flash chromatography on silica gel with the eluent 0-3% ethyl acetate in hexane to afford z-stilbene 10a (0.86 g, 39%) which crystallized as a colorless solid from hexane: mp 122-124° C.: $^1$H-NMR (300 MHz, CDCl$_3$) δ 1.07 (s, 9H, 3.45 (s, 3H), 3.55 (s, 3H), 3.79 (s, 3H), 6.21 (d, 1H, J=12 Hz), 6.31 (d, 1H, J=12 Hz), 6.59 (d, 1H, J=7.8 Hz), 6.72 (s, 2H), 6.77 (dd, 1H, J=7.8, 1.5 Hz), 7.19 (d, 1H, J=1.8 Hz), 7.40-7.20 (m, 6H), 7.64 (d, 4H, J=7.5 Hz); $^{13}$C-NMR (75 MHz, CDCl$_3$) δ 19.68, 26.62, 55.05, 55.56, 60.33, 91.94, 111.72, 113.09, 120.78, 122.43, 126.73, 127.33, 129.32, 130.28, 130.93, 133.54, 135.17, 144.70, 149.82, 151.82, HRMS calcd for C$_{33}$H$_{36}$IO$_4$Si 651.1428 [M+H]$^+$, found 651.1474; Anal. calcd for C$_{33}$H$_{35}$IO$_4$Si C, 60.92; H, 5.45. Found, C, 60.79; H, 5.67%.

Further elution gave E-stilbene 10b (0.96 g, 43%) that crystallized from hexane as a colorless solid; mp 98-99° C.; $^1$H-NMR (300 MHz, CDCl$_3$) δ 1.14 (s, 9H), 3.55 (s, 3H), 3.82 (s, 3H), 3.82 (s, 3H), 3.89 (s, 3H), 6.43 (d, 1H, J=15.9 Hz), 6.7-1.76 (m, 2H), 6.86-6.95 (m, 3H), 7.33-7.42 (m, 6H); $^{13}$C-NMR (100 MHz, CDCl$_3$) δ 19.81, 26.67, 55.28, 60.50, 92.65, 110.22, 112.11, 117.70, 120.56, 124.58, 127.52, 128.45, 128.68, 129.60, 129.77, 133.64, 135.38, 135.82, 145.18, 148.13, 150.56, 152.49; HRMS calcd for C$_{33}$H$_{36}$IO$_4$Si 651.1428 [M+H]$^+$, found 651.1400; Anal. calcd for C$_{33}$H$_{35}$IO$_4$Si, C, 60.92; H, 5.42, found C, 60.88; H, 5.63%.

Method B. Butyllithium (4.5 mL, 11.3 mmol) was added to a stirred and cooled (−70° C.) suspension of phosphonium bromide 6 in dry THF (100 mL). The solution was stirred for 30 min at −70° C. then 6 hours at room temperature. Water (50 mL) was added and the reaction mixture was extracted with EtOAc (3×100 mL), the extract dried, filtered and concentrated. The oil obtained was subjected to flash chromatography on silica eluent 0-3% ethyl acetate in hexane to afford Z-stilbene 10a (1.4 g, 21%) as a colorless solid: mp 122-124° C.

3,5-diiodo-4,4'-dimethoxy-3'-O-tert-butyl-diphenylsilyl-stilbene and 3,5-diiodo-4,4'-dimethoxy-3'-O-tert-butyl-diphenylsilyl-E-stilbene Method A. Phosphonium bromide 6 (2.77 g, 3.87 mmol) (8) was dissolved in DCM at 0° C. When sodium hydride (60% dispersion in mineral oil, 0.31 g, 7.7 mmol) was added, the mixture turned orange. Aldehyde (1.0 g, 2.57 mmol) was added and stirring was continued for 7.5 hrs. The reaction was terminated by adding water (50 mL) and extracted with DCM (3×50 mL). The organic extract was dried, filtered and concentrated. The oily residue was subjected to flash chromatography on silica gel using hexane as eluent to give an isomeric mixture of the title compounds (71% yield, 1.35 g). Further elution gave E-isomer (0.10 g, 5%) as a colorless oil in pure form: $^1$H-NMR (300 MHz, CDCl$_3$) δ 1.14 (s, 9H), 3.56 (s, 3H), 3.84 (s, 3H), 6.33 (d, 1H, J 15.9 Hz), 6.72 (d, 1H, J 8.4Hz), 6.73 (d, 1H J 15.9 Hz), 6.72 (d, 1H, J 8.4 Hz, ArH), 6.85 (d, 1H, J 2.1 Hz), 6.92 (dd, 1H, J 1.8 Hz and J 8.4 Hz), 7.34-7.46 (m, 6H) and 7.72-7.75 (m, 6H); $^{13}$C-NMR (100 MHz, CDCl$_3$) δ 19.82, 26.69, 55.30, 60.77, 90.59, 112.09, 117.73, 120.83, 122.47, 127.55, 129.38, 129.65, 129.99, 133.58, 135.40, 137.15, 137.73, 145.22, 150.84 and 157.55; and HRMS calcd for $C_{32}H_{33}I_2O_3Si$ 747.0289 [M+H]$^+$, found 747.0442.

Method B. Butyllithium (0.6 mL, 1.47 mmol) was added to a stirred and cooled (−10° C.) suspension of phosphoniurn bromide 6 (1.01 g, 1.4 mmol) in dry THF (80 mL). The orange-red solution was stirred for 10 minutes at room temperature. Aldehyde (0.50 g, 1.33 mmol) was added and the reaction mixture color changed from red to yellow. Stirring was continued at room temperature for 10 minutes, ice water (100 mL) was added and the mixture extracted with EtOAc (3×100 mL). The extract was washed with water (100 mL), dried, filtered and concentrated. The resulting oil was partially separated by flash chromatography on silica gel using hexane-EtOAc (100:1) as eluent to give an isomeric mixture in a ratio approximately 1:1.9, (cis:trans, 0.90 g, 90%).

3-Iodo-4,4',5-trimethoxy-3'-hydroxy-z-stilbene (14a). To a solution of silyl ether 7a (1.30 g, 1.99 mmol) in THF was added tetrabutylammonium flouride (2.2 mL, 2.2 mmol). The mixture was stirred under Ar in the dark for 10 min. and the reaction was terminated by the addition of water (5 mL), the product was extracted with EtOAc (3×15 mL), and the extract dried, filtered and concentrated. The crude product was separated by silica gel column chromatography using 1:4 ethyl acetate-hexane as eluent to give stilbene 14a (0.70 g, 85%) as colorless solid: mp 92-94° C., IR 3543, 3011, 2937, 2841, 1510, 1273, 1001, 908, 732 cm$^{-1}$; $^1$H-NMR (300 MHz, CDCl$_3$) δ 3.61 (s, 3H), 3.81 (s, 3H), 3.84 (s, 3H), 6.32 (d, 1H, J=12 Hz), 6.34 (s, 1H), 6.56 (d, 1H, J=12 Hz), 6.75 (s, 1H), 6.83 (d, 1H, J=1.8 Hz), 6.85 (s, 3H), 7.25 (d, 1H, J=1.5 Hz); $^{13}$C-NMR (75 MHz, CDCl$_3$) δ 55.56, 55.82, 60.33, 91.78, 110.50, 113.11, 115.00, 120.91, 126.96, 129.94, 130.28, 135.93 145.29, 146.10, 147.67, 151.79; HRMS calcd for $C_{17}H_{18}IO_4$ 413.0259 [M+H]$^+$, found 413.0250. Anal. calcd for $C_{17}H_{17}IO_4$ C, 49.53; H, 4.16. Found C, 49.38; H, 4.24%.

3-Iodo-4,4',5-trimethoxy-3'-hydroxy-E-stilbene (9b). The trans isomer 14b (0.29 g, 98%) was obtained from silyl ether 10b (0.46 g, 0.7 mmol) as described above for the synthesis of the cis isomer 14a. Separation by column chromatography (7:3 hexane-ethyl acetate as eluent) gave E-isomer 14b (0.29 g, 98%) as colorless solid: mp 111-113° C.; $^1$H-NMR (300 MHz, CDCl$_3$) δ 3.84 (s, 3H), 3.87 (s, 3H), 3.88 (s, 3H, 5.85 (bs, 1H), 6.77 (d, 1H, J=16.5 Hz), 6.89 (d, 1H, J=16.5 Hz), 6.82 (s, 1H), 6.96 (s, 1H), 6.93 (d, 1H, J=2.4 Hz), 7.11 (d, 1H, J=1.5 Hz), 7.46 (d, 1H, J=1.5 Hz); $^{13}$C-NMR (75 MHz, CDCl$_3$) δ 55.85, 60.41, 92.56, 110.40, 110.63, 111.77, 119.28, 124.97, 128.36, 128.70, 130.15, 135.71, 145.71, 146.56, 148.11, 152.44; HRMS calcd for $C_{17}H_{18}IO_4$ 413.0257 [M+H]$^+$, found 413.0250. Anal. calcd for $C_{17}H_{17}IO_4$ C, 49.53; H, 4.16. Found, C, 49.38; H, 4.24%.

3,5-diiodo-4,4'-dimethoxy-3'-hydroxy-Z-stilbene 22a and 3,5-diiodo-4,4'-dimethoxy-3'-hydroxy-E-stilbene 22b These stilbenes were obtained from the z and E silyl ether mixture 21ab (1.35 g, 1.81 mmol) as described above for the synthesis of cis-isomer 14a. The oily mixture was separated by column chromatography with 2:1 hexane-EtOAc as eluent to provide cis-isomer 22a as an oil (0.45 g, 49%): $^1$H-NMR (300 MHz, CDCl$_3$) δ 3.85 (s, 3H), 3.89 (s, 3H), 5.54 (s, 1H), 6.26 (d, 1H, J=12 Hz), 6.49 (d, 1H, J=12 Hz), 6.74 (s, 2H), 6.82 (s, 1H) and 7.67 (s, 2H); $^{13}$C-NMR (125 z, CDCl$_3$) δ 55.98, 60.73, 89.98, 110.46, 114.87, 120.98, 125.08, 29.47, 131.57, 137.37, 139.96, 145.42, 146.21, 157.50. HRMS calcd for $C_{16}H_{15}I_2O_3$ 508.9113 [M+H]$^+$, found 508.9111. Anal. calcd for $C_{16}H_{14}I_2O_3$ C, 37.82; H, 2.78. Found, C, 37.80; H, 2.83.

Further elution led to the E-stilbene 22b (0.46 g, 50% yield) as a colorless solid which was crystallized from hexane: mp 127-129° C.; $^1$H-NMR (300 MHz, CDCl$_3$) δ 3.86 (s, 3H), 3.91 (s, 3H), 5.62 (s, 1H), 6.71 (d, 1H, J=16.5 Hz), 6.83 (d, 1H, J=8.1 Hz), 6.90 (d, 1H, J=17.1 Hz), 6.95 (d, 1H, J=8.4 Hz), 7.10 (d, 1H, J=2.4 Hz) and 7.85 (s, 2H, H-2); $^{13}$C-NMR (75 MHz, CDCl$_3$) δ 55.51, 60.30, 90.17, 100.17, 100.21, 110.18, 111.35, 119.17, 122.56, 129.63, 129.81, 136.82, 137.19, 146.34 and 157.25; HRMS calcd for $C_{16}H_{15}I_2O_3$ 508.9113 [M+H]$^+$, found 508.9119. Anal. calcd for $C_{16}H_{14}I_2O_3$ C, 37.82; H, 2.78. Found, C, 38.01; H, 2.91.

3,5-diiodo-4,4'-dimethoxy-3'-acetyl-z-stilbene (22c)

An appropriate phenol 22a (0.45 g) was dissolved in pyridine (3 mL), acetic anhydride (170 µL) and stirred for 2 hrs. The mixture was concentrated under reduced pressure from toluene (3×10 mL). The residue was diluted with EtOAc (30 mL), washed successively with water (10 mL), NaHCO$_3$ (10% aq. sol., 10 mL), dried, and the solution filtered and concentrated. The acetate was further purified by flash chromatography on silica using 1:24 hexane-EtOAc:hexane as eluent to afford acetate 22c (0.20 g, 41%) as a colorless solid: recrystallized from hexane mp 121-122° C.; $^1$H-NMR (300 MHz, CDCl$_3$) δ 2.29 (s, 3H), 3.83 (s, 3H), 3.85 (s, 3H), 6.29 (d, 1H, J=12 Hz), 6.48 (d, 1H, J=12 Hz), 6.85 (d, 1H, J=8.7 Hz), 6.93 (d, 1H, J=2.43), 7.06 (d, 1H, J=1.5), 7.09 (d, 1H, J=2.4 Hz) and 7.67 (s, 2H); $^{13}$C-NMR (125 MHz, CDCl$_3$) 20.66, 55.94, 60.72, 90.11, 112.16, 123.25, 125.41, 127.47, 128.85, 130.64, 137.10, 139.54, 139.89, 150.69, 157.67 and 168.79; HRMS calcd for $C_{19}H_{20}I_2O_5$ 582.9479 [M+CH$_3$OH]$^+$, found 582.9482; Anal. calcd for $C_{18}H_{16}I_2O_4$ C, 39.30; H, 2.93. Found C, 39.30; H, 3.13%.

3-iodo-4,4',5-trimethoxy-3'-acetyl-Z-stilbene

An appropriate phenol (0.1 g, 0.24 mmol) was dissolved in 3 mL anhydrous pyridine. Acetic anhydride (50 µL, 0.51 mmol) was added with cat DMAP. The mixture was stirred for 90 minutes. The reaction was terminated by the addition of 5 mL CH$_3$OH. The mixture was diluted with toluene and concentrated under reduced pressure. It was purified on flash chromatography on silica gel using EtOAc:hexane (1:9) as eluent to give a white solid (0.1 mg, 91%). The solid was crystallized from hexane: mp 103-104° C.; $^1$H-NMR (300 MHz, CDCl$_3$) δ 2.27 (s, 3H), 3.61 (s, 3H), 3.81 (s, 6H), 6.38 (d, 1H, J=12 Hz), 6.48 (d, 1H, J=12 Hz), 6.77 (d, 1H, J=1.8 Hz), 6.83 (d, 1H, J=8.4 Hz), 6.96 (d, 1H, J=1.5 Hz), 7.09 (dd, 1H, J=8.4 Hz, J=2.4 Hz), and 7.26 (s, 1H); $^{13}$C-NMR (125 MHz, CDCl$_3$) δ 20.61, 55.67, 55.93, 60.44, 92.07, 112.07, 112.92, 123.17, 127.63, 127.74, 129.39, 129.65, 103.97, 134.96, 139.49, 147.99, 150.39, 152.05 and 168.81; HRMS calcd for $C_{19}H_{20}IO_5$ 455.0355 [M+H]$^+$, found 455.0356. Anal. calcd for $C_{19}H_{19}IO_5$ C, 50.24; H, 4.22. Found, C, 49.67; H, 4.18%.

Dibenzyl 3,5-diiodo-4,4'-dimethoxy-z-stilbene 3'-O-phosphate (23)

An appropriate dibenzyl phosphate (0.38 g, 55% yield) was obtained (0.46 g, 0.91 mmol) as described above for the synthesis of iodide 10a. Colorless oil: bp dec 220° C.; $^1$H-NMR (300 MHz, CDCl$_3$) δ 3.78 (s, 3H), 3.81 (s, 6H), 5.13 (s, 2H), 5.16 (s, 2H), 6.28 (d, 1H, J=12 Hz), 6.42 (d, 1H, J=12 Hz), 6.78 (d, 1H, J=9 Hz), 7.00 (d, 1H, J=8.7 Hz), 7.07 (s, 1H), 7.33 (s, 10H) and 7.64 (s, 2H); $^{13}$C-NMR (100 MHz, CDCl$_3$) δ 55.96, 60.71, 69.83, 69.89, 90.15, 112.40, 122.23, 122.26, 125.60, 126.20, 126.21, 127.93, 128.49, 128.55, 130.66, 137.12, 139.92 and 157.68; HRMS calcd for $C_{30}H_{28}I_2O_6P$ 768.9713 [M+H]$^+$, found 768.9699; $^{31}$P-NMR (162 MHz, CDCl$_3$) δ −5.51.

General Procedures for Syntheses of the Phosphoric Acids and Derivatives

Method A. Each of the metal cation phosphate salts was obtained by the procedure outlined herein for preparing the potassium salt 20c, except for the metal counterions introduced by treatment of the phosphoric acid using either lithium hydroxide or sodium methoxide.

Method B. Dowex-50W (2 g) (HCR-W2) was placed in a column and washed successively with CH$_3$OH (50 mL), 1 N HCl (until pH 1), water (until pH 7), base/amine/amino acid (until pH 7-14) and water (until pH 7). The column was recycled. The potassium salt or its corresponding diiodo phosphate salt (about 25 mg) was dissolved in de-ionized water (1 mL) and applied to a Dowex-50W (HCR-W2) resin column (bearing the appropriate amine or amino acid methyl ester) and developed with approximately 40 mL of water. The eluent was concentrated by freeze drying to give the required cation derivative.

Method C. Amino Acid Methyl Esters. The amino acid methyl ester hydrochloride was neutralized in CH$_3$OH solution by adding potassium carbonate. Ether was added to precipitate the potassium chloride and the solution was filtered and concentrated. The amino acid methyl ester residue was then applied to the Dowex-50W (HCR-W2) resin column as described in Method B.

Potassium 3-iodo-4,4',5-trimethoxy-z-stilbene 3'-O-phosphate (20c)

Trimethylbromosilane (277 μL, 1.8 mmol) was added to a cooled (0° C.) solution of phosphate 9a in DCM (40 mL). After stirring for 90 minutes, sodium thiosulfate (10%/n aq., 10 mL) was added and the mixture was stirred for an additional 1 minute. The phases were separated and the aqueous phase extracted with DCM (20 mL), followed by EtOAc (2×20 mL). The combined organic extracts were dried, filtered and concentrated to afford the phosphoric acid intermediate as a clear oil. After drying (high vacuum) for 1 hour, the oil was dissolved in CH$_3$OH (10 mL), cooled to 0° C., and KOH (1.8 mL, 1 M sol. in CH$_3$OH) was added. The mixture was stirred for 20 minutes, the precipitate was collected and triturated with ether to afford the potassium salt as a colorless solid: mp 197-198° C. (dec); $^1$H-NMR (300 MHz, D$_2$O) δ 3.51 (s, 3H), 3.64 (s, 3H), 3.71 (s, 3H), 6.33 (d, 1H, J=12 Hz), 6.51 (d, 1H, J=12 Hz), 6.70 (s, 2H), 6.84 (s, 1H) and 7.22 (s, 2H); and $^{31}$P-NMR (162 MHz, D$_2$O) δ 0.94.

Sodium 3-iodo-4,4',5-trimethoxy-z-stilbene 3'-O-phosphate (20a)

Isolated as a colorless solid: mp 194-195° C. (dec); $^1$H-NMR (300 MHz, D$_2$O) δ 3.50 (s, 3H), 3.67 (s, 3H), 3.68 (s, 3H), 6.50 (d, 1H, J=12 Hz), 6.70 (d, 1H, J=12 Hz), 6.72 (s, 1H), 6.77 (s, 1H), 6.79 (s, 1H), 7.01 (s, 1H) and 7.13 (s, 1H).

Lithium 3-iodo-4,4',5-trimethoxy-z-stilbene 3'-O-phosphate (11c)

Discovered as a colorless solid: mp 245-275° C. (dec); $^1$H-NMR (400 MHz, D$_2$O) δ 3.50 (s, 3H), 3.62 (s, 3H), 3.66 (s, 3H), 6.33 (d, 1H, J=12 Hz), 6.49 (d, 1H, J=12 Hz), 6.70 (s, 2H), 6.83 (s, 1H), 7.20 (s, 1H) and 7.22 (s, 1H).

Morpholine 3-iodo-4,4',5-trimethoxy-Z-stilbene 3'-O-phosphate

Another colorless oil: $^1$H-NMR (300 MHz, D$_2$O) δ 3.11-3.15 (m, 8H), 3.50 (s, 3H), 3.63 (s, 3H), 3.68 (s, 3H), 3.77-3.81 (m, 8H), 6.33 (d, 1H, J 12 Hz), 6.50 (d, 1H, J 12 Hz), 6.73 (s, 2H), 6.82 (s, 1H), 7.18 (s, 1H) and 7.20 (s, 1H).

Piperidene 3-iodo-4,4',5-trimethoxy-z-stilbene 3'-O-phosphate

Colorless oil: $^1$H-NMR (300 MHz, D$_2$O) δ 1.51 (m, 4H), 1.62 (m, 8H), 3.00 (t, 8H, J=6 Hz), 3.51 (s, 3H), 3.63 (s, 3H), 3.67 (s, 3H), 6.34 (d, 1H, J=12.6 Hz), 6.51 (d, 1H, J=12.6 Hz), 6.72 (s, 2H), 6.83 (s, 1H) and 7.21 (s, 1H).

Glycine-OMe 3-iodo-4,4',5-trimethoxy-z-stilbene 3'-O-phosphate

Obtained as a colorless solid: mp 74-78° C.; $^1$H-NMR (300 MHz, D$_2$O) δ 3.48 (s, 3H), 3.61 (s, 3H), 3.67 (s, 3H), 3.68 (s, 3H), 3.76 (s, 2H), 6.30 (d, 1H, J=12 Hz), 6.46 (d, 1H, J=12 Hz), 6.69-0.77 (m, 3H), 7.10 (s, 1H) and 7.16 (s, 1H).

Tryptophan-OMe 3-iodo-4,4',5-trimethoxy-z-stilbene 3'-O-phosphate

Colorless solid: mp 108-112° C.; $^1$H-NMR (300 MHz, DMSO) δ 3.19 (d, 2H, J=6.3 Hz), 3.56 (s, 3H), 3.61 (s, 3H), 3.66 (s, 3H), 3.70 (s, 3H), 4.09 (t, 1H, J=6 Hz), 6.35 (d, 1H, J=12 Hz), 6.47 (d, 1H, J=12 Hz), 6.81-6.85 (m, 2H), 6.98 (t, 1H, J=7.2 Hz), 7.07 (t, 1H, J=8.1 Hz), 7.18 (s, 1H), 7.22 (s, 1H), 7.34 (d, 1H, J=8.1 Hz), 7.40 (s, 1H) and 7.46 (d, 1H, J=7.2 Hz).

Tris 3-iodo-4,4',5-trimethoxy-Z-stilbene 3'-O-phosphate

Colorless solid: mp 75-81° C.; $^1$H-NMR (300 MHz, DMSO) δ 3.42 (s, 9H), 3.57 (s, 3H), 3.67 (s, 3H), 3.70 (s, 3H), 6.35 (d, 1H, J=12 Hz), 6.4.8 (d, 1H, J=12 Hz), 6.76 (d, 1H, J=8.4 Hz), 6.81 (d, 1H, J=8.7 Hz), 6.92 (s, 1H), 7.22 (s, 1H) and 7.42 (s, 1H).

Potassium 3,5-diiodo-4,4'dimethoxy-z-stilbene 3'-O-phosphate

Phosphate (0.20 g, 80%) was obtained from appropriate ester 9c (0.29 g, 0.38 mmol) as described above for the synthesis of 20c, except the phosphoric acid was insoluble in EtOAc and DCM, so the aqueous phase was extracted with butyl alcohol (3×25 mL). The potassium salt was a colorless solid: mp 210-215° C. (dec); $^1$H-NMR (300 MHz, D$_2$O) δ 3.69 (s, 6H), 6.27 (d, 1H, J=12 Hz), 6.49 (d, 1H, J=12 Hz), 6.64 (s, 2H), 7.20 (s, 1H) and 7.62 (s, 2H); $^{31}$P-NMR (162 MHz, D$_2$O): δ 0.973.

Sodium 3,5-diiodo-4,4'dimethoxy-z-stilbene 3'-O-phosphate

Obtained as a colorless solid: mp 215-234° C. (dec); $^1$H-NMR (300 MHz, D$_2$O) δ 3.69 (s, 3H), 3.72 (s, 3H), 6.29 (d, 1H, J=12 Hz), 6.49 (d, H, J=12 Hz), 6.69 (s, 2H), 7.20 (s, 1H) and 7.64 (s, 2H).

Lithium 3,5-diiodo-4,4'dimethoxy-z-stilbene 3'-O-phosphate

A colorless solid melting at 250-270° C. (dec); $^1$H-NMR (300 MHz, D$_2$O) δ 3.68 (s, 3H), 3.71 (s, 3H), 6.28 (d, 1H, J=12 Hz), 6.49 (d, 1H, J=12 Hz), 6.68 (s, 2H), 7.19 (s, 1H) and 7.64 (s, 2H). $^{31}$P NMR (162 MHz, D$_2$O) δ 0.96.

Morpholine 3,5-diiodo-4,4'dimethoxy-z-stilbene 3'-O-phosphate

Colorless waxy solid; mp 75-80° C.; $^1$H-NMR (300 MHz, DMSO) δ 2.96-2.99 (m, 8H), 3.74-3.77 (m, 8H), 3.82 (s, 3H), 3.83 (s, 3H), 6.43 (d, 1H, J=12.5 Hz), 6.60 (d, 1H, J=12.5 Hz), 6.86 (d, 1H, J=8.2 HZ), 6.93 (d, 1H, J=8.2 Hz), 7.49 (s, 1H) and 7.78 (s, 2H).

Piperidine 3,5-diiodo-4,4'dimethoxy-z-stilbene 3'-O-phosphate

Isolated as a colorless oil; $^1$H-NMR (300 MHz, DMSO) δ 1.51 (br s, 12H), 2.79-2.81 (m, 8H), 3.70 (s, 3H), 3.72 (s, 3H), 6.31 (d, 1H, J=12 Hz), 6.49 (d, 1H, J=12 Hz), 6.73 (d, 1H, J=8.4 Hz), 6.80 (d, 1H, J=8.4 Hz), 7.40 (s, 1H) and 7.61 (s, 1H).

Glycine-OMe 3,5-diiodo-4,4'dimethoxy-z-stilbene 3'-O-phosphate

Colorless solid; mp 90-97° C.; $^1$H-NMR (300 MHz, DMSO) δ 3.61 (s, 4H), 3.68 (s, 6H), 3.70 (s, 3H), 3.72 (s, 3H), 6.31 (d, 1H, J=12 Hz), 6.49 (d, 1H, J=12 Hz), 6.72 (d, 1H, J=9.6 Hz), 6.80 (d, 1H, J=8.1 Hz), 7.37 (s, 1H) and 7.67 (s, 1H).

Tryptophan-OMe 3,5-diiodo-4,4'dimethoxy-z-stilbene 3'-O-phosphate

Collected as a colorless solid; melting at 125-130° C.; $^1$H-NMR (300 MHz, DMSO) δ 3.34 (d, 1H, J=6.5 Hz), 3.36 (d, 1H, J=6.5 Hz), 3.66 (s, 3H), 3.70 (s, 3H), 3.72 (s, 3H), 4.32 (t, 1H, J=6.5 Hz), 6.31 (d, 1H, J=12 Hz), 6.48 (d, 1H, J=12 Hz), 6.78-0.81 (m, 2H), 7.01 (s, 1H), 7.05 (t, 1H, J=7 Hz), 7.13 (t, 1H, J=7 Hz), 7.39 (d, 1H, J=7.5 Hz) 747 (d, 1H, J=8 Hz) and 7.60 (s, 1H).

Tris 3,5-diiodo-4,4'dimethoxy-z-stilbene 3'-O-phosphate

Colorless solid; mp 115-120° C.; $^1$H-NMR (300 MHz, DMSO) δ 3.34 (s, 18H), 3.69 (s, 3H), 3.71 (s, 3H), 6.30 (d, 1H, J=12 Hz), 6.47 (d, 1H, J=12 Hz), 6.70 (d, 1H, J=8.1 Hz), 6.78 (d, 1H, J=8.1 Hz), 7.37 (s, 1H) and 7.67 (s, 2H).

Cancer Cell Line Procedures

Inhibition of human cancer cell growth was assessed using the National Cancer Institute's standard sulforhodamine B assay. After 48 hours, the plates were fixed with trichloracetic acid, stained with sulforhodamine B and read with an automated microplate reader. A growth inhibition of 50% (GI$_{50}$ or the drug concentration causing a 50% reduction in the net protein increase) was calculated from optical density data with Immunosoft software. Inhibition of the mouse leukemia P388 cells was assessed in a 10% horse serum/Fisher medium solution for 24 hours, followed by a 48 hour incubation with serial dilutions of the compounds. Cell growth inhibition (ED$_{50}$) was then calculated using a Z1 Beckman/Coulter particle counter.

Tubulin Evaluations: Tubulin polymerization was evaluated by turbidimetry at 35 nm using Beckman DU7400/7500 spectrophotometers as known to one of skill in the art. Varying concentrations of the compound were preincubated with 10 μM. Incubation was for 10 minutes at 37° C.

Antiangiogenesis

HUVEC Procedures

In vitro Matrigel antiangiogenesis assays were implemented according to the Developmental Therapeutics Program NCI/NIH protocols known to one of skill in the art. Matrigel, a basement membrane matrix, was obtained from BD Biosciences. Growth inhibition and cord formation assays were Conducted using human umbilical vein endothelial cells obtained from GlycoTeCh. HUVEC cells were grown in EGM-2 medium.

Cord Formation Assay

An aliquot of sixty microliters was placed in each well of an ice-cold 96-well plate. The plates were then left for 15 minutes at room temperature, then incubated for 30 minutes at 37° C. to permit the matrigel to polymerize. Meanwhile, HUVEC cells were harvested and diluted to a concentration of 2×10$^5$ cells/ml. A solution of 100 μL containing the compounds to be tested was added next. After 24 hours incubation, pictures were taken for each concentration using an inverted Nikon Diaphot microscope and D100 digital camera. Drug effect was assessed, compared to untreated controls, by measuring the length of cords formed and number of junctions.

The standard sulforhodamine B assay (see Cancer Cell Line Procedures above) was used to evaluate results using HUVEC cells. $IC_{50}$ or $ED_{50}$ (drug concentration causing 50% inhibition) was calculated from the plotted data.

Administration

Dosages

The dosage to be administered to humans and other animals requiring treatment will depend upon the identity of the neoplastic disease or microbial infection; the type of host involved, including its age, health and weight; the kind of concurrent treatment, if any; the frequency of treatment and therapeutic ratio. Hereinafter are described various possible dosages and methods of administration, with the understanding that the following are intended to be illustrative only, and that the actual dosages to be administered, and methods of administration or delivery may vary therefrom. The proper dosages and administration forms and methods may be determined by one of skill in the art.

Illustratively, anticipated dosage levels of the administered active ingredients may be in the following ranges: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/k of host body weight.

Expressed in terms of concentration, an active ingredient can be present in the compositions of the present invention for localized use about the cutis, intranasally, pharyngolaryngeally, bronchially, intravaginally, rectally, or ocularly in concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are intended to be presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient. Other dosage forms known in the art may be used.

For oral administration either solid or fluid unit dosage forms may be prepared.

Powders may be prepared by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules may be produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules may be prepared by machine encapsulation of a slurry of active ingredients with an acceptable vegetable oil, light liquid petrolatum or other inert oil or triglyceride or other pharmaceutically acceptable carrier.

Tablets may be made by preparing a powder mixture, granulating or slugging, adding a lubricant and pressing into tablets. The powder mixture may be prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture may be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, for protection of the tablet itself and/or to ease swallowing, the tablet can be provided with a pharmaceutically acceptable coating such as a sealing coat or enteric coat of shellac, a coating of sugar and methylcellulose and polish coating of carnauba wax.

Fluid unit dosage forms for oral administration such as in syrups, elixirs and suspensions may be prepared wherein each teaspoonful of composition contains a predetermined amount of an active ingredient for administration.

The water-soluble forms may be dissolved in an aqueous vehicle together with sugar, flavoring agents and preservatives to form a syrup. An elixir is prepared by using a hydroalcoholic vehicle with suitable sweeteners together with a flavoring agent. Suspensions may be prepared of the insoluble forms with a suitable vehicle with the aid of a pharmaceutically acceptable suspending agent such as acacia, tragacanth, methylcellulose and the like.

For parenteral administration, fluid unit dosage forms may be prepared utilizing an active ingredient and a sterile vehicle, for examples water. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions may be prepared in substantially the same manner except that an active ingredient is suspended in the vehicle instead of being dissolved and sterilization cannot be accomplished by filtration. The active ingredient may be sterilized by exposure to ethylene oxide before suspending in the sterile vehicle. Advantageously, a pharmaceutically acceptable surfactant or wetting agent may be included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal installation, a fluid unit dosage form may be prepared utilizing an active ingredient and a suitable pharmaceutical vehicle, such as purified water, a dry powder, can be formulated when insufflation is the administration of choice.

For use as aerosols, the active ingredients may be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents may be prepared in such unit dosage form with the employment of pharmaceutical materials which themselves are available in the art and can be prepared by established procedures. The following preparations are illustrative of the preparation of the unit dosage forms of the present invention, and not as a limitation thereof. Shown in the following are examples of dosage forms for the compounds of the present invention, in which the notation "active ingredient" signifies the compounds described herein.

Composition "A"

Hard-Gelatin Capsules

One thousand two-piece hard gelatin capsules for oral use, each capsule containing 200 mg of an active ingredient may be prepared from the following types and amounts of ingredients:

| Active ingredient, micronized | 200 g |
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

Using the procedure above, capsules may be similarly prepared containing an active ingredient in 50, 250 and 500 mg amounts by substituting 50 g, 250 g and 500 g of an active ingredient for the 200 g used above.

Composition "B"

Soft Gelatin Capsules

One-piece soft gelatin capsules for oral use, each containing 200 mg of an active ingredient, finely divided by means of an air micronizer, may prepared by first suspending the compound in 0.5 ml of corn oil to render the material capsulatable and then encapsulating in the above manner.

Composition "C"

Tablets

One thousand tablets, each containing 200 mg of an active ingredient, may be prepared from the following types and amounts of ingredients:

| Active ingredient, micronized | 200 g |
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 mg of the active ingredient.

Using the procedure above, tablets may similarly prepared containing an active ingredient in 250 mg and 100 mg amounts by substituting 250 g and 100 g of an active ingredient for the 200 g used above.

Composition "D"

Oral Suspension

One liter of an aqueous suspension for oral use, containing in each teaspoonful (5 ml) dose, 50 mg of an active ingredient, may be prepared from the following types and amounts of ingredients:

| Active ingredient, micronized | 10 g |
| Citric acid | 2 g |
| Benzoic acid | 1 g |
| Sucrose | 790 g |
| Tragacanth | 5 g |
| Lemon Oil | 2 g |
| Deionized water, q.s. | 1000 ml |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

Composition "E"

Parenteral Product

A sterile aqueous suspension for parenteral injection, containing 30 mg of an active ingredient in each milliliter for treating a neoplastic disease, may be prepared from the following types and amounts of ingredients:

| Active ingredient, micronized | 30 g |
|---|---|
| POLYSORBATE 80 | 5 g |
| Methylparaben | 2.5 g |
| Propylparaben | 0.17 g |
| Water for injection, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

Composition "F"

Suppository, Rectal and Vaginal

One thousand suppositories, each weighing 2.5 g and containing 200 mg of an active ingredient may be prepared from the following types and amounts of ingredients:

| Active ingredient, micronized | 15 g |
|---|---|
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

Composition "G"

Intranasal Suspension

One liter of a sterile aqueous suspension for intranasal instillation, containing 20 mg of an active ingredient in each milliliter, may be prepared from the following types and amounts of ingredients:

| Active ingredient, micronized | 15 g |
|---|---|
| POLYSORBATE 80 | 5 g |
| Methylparaben | 2.5 g |
| Propylparaben | 0.17 g |
| Deionized water, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

Composition "H"

Powder

Five grams of active ingredient in bulk form is finely divided by means of an air micronizer The micronized powder is placed in a shaker-type container.

Composition "I"

Oral Powder

One hundred grams of an active ingredient in bulk form may be finely divided by means of an air micronizer. The micronized powder is divided into individual doses of 200 mg and packaged.

Composition "J"

Insulation

One hundred grams of an active ingredient in bulk form is finely divided by means of an air micronizer.

It is of course understood that such modifications, alterations and adaptations as will readily occur to the artisan confronted with this disclosure are intended within the spirit of the present invention.

TABLE I

Human cancer cell line inhibition ($GI_{50}$ μg/mL) and murine P388 lymphocytic leukemia inhibitory activity ($ED_{50}$ μg/ml) of halocombstatins and other compounds.

| Compound | Leukemia P388 | Pancreas-a BXPC-3 | Breast adn MCF-7 | CNS SF268 | Lung-NSC NCI-H460 | Colon KM20L2 | Prostate DU-145 |
|---|---|---|---|---|---|---|---|
| 1a | 0.0003 | 0.39 | — | <0.001 | 0.0006 | 0.061 | 0.0008 |
| 1b | 0.0004 | — | — | 0.036 | 0.029 | 0.034 | — |
| 2a | 0.251 | 4.4 | — | — | 0.74 | 0.061 | 0.17 |
| 2b | <0.01 | 1.5 | 0.024 | 0.036 | 0.038 | 0.53 | 0.034 |
| 3a | 0.257 | 2.3 | 0.49 | 0.0083 | 0.19 | 1.2 | 0.0043 |
| 3b | 0.305 | 2.8 | 0.92 | 0.052 | 0.45 | 3.5 | 0.048 |
| 11a | <0.01 | 0.016 | <0.01 | <0.01 | <0.01 | 1.1 | <0.01 |
| 11b | 0.253 | 2.2 | 0.051 | 0.35 | 0.18 | 0.53 | 0.18 |
| 12a | <0.01 | 0.043 | <0.001 | <0.001 | <0.001 | 0.15 | <0.001 |
| 12b | 0.027 | 0.59 | 0.041 | 0.048 | 0.034 | 1.4 | 0.038 |
| 13a | <0.01 | 0.16 | <0.001 | <0.001 | <0.001 | 0.086 | <0.001 |
| 13b | 0.0174 | 1.6 | 0.14 | 0.18 | 0.15 | 1.2 | 0.13 |

TABLE I-continued

Human cancer cell line inhibition (GI$_{50}$ μg/mL) and murine P388 lymphocytic leukemia inhibitory activity (ED$_{50}$ μg/ml) of halocombstatins and other compounds.

| Compound | Leukemia P388 | Pancreas-a BXPC-3 | Breast adn MCF-7 | CNS SF268 | Lung-NSC NCI-H460 | Colon KM20L2 | Prostate DU-145 |
|---|---|---|---|---|---|---|---|
| 14a | <0.01 | 0.11 | 0.00022 | 0.00035 | 0.00019 | 0.15 | 0.00052 |
| 14b | 0.189 | 2.7 | 0.18 | 0.55 | 0.21 | 1.7 | 0.27 |
| 18a | 0.0298 | 0.59 | 0.0044 | 0.0051 | 0.0094 | 1.5 | 0.0036 |
| 19a | <0.01 | 0.093 | 0.0041 | 0.0034 | 0.0028 | 0.23 | 0.0046 |
| 19b | <0.01 | 0.13 | 0.0039 | 0.0030 | 0.0026 | 0.11 | 0.0066 |
| 19c | <0.01 | 0.20 | 0.0035 | 0.0032 | 0.0029 | 0.24 | 0.0028 |
| 19d | <0.01 | 0.15 | 0.0044 | 0.0064 | 0.0066 | 0.48 | 0.0079 |
| 19e | <0.01 | 0.56 | 0.043 | 0.023 | 0.041 | 2.6 | 0.042 |
| 19f | 0.288 | <0.001 | 0.0022 | 0.0022 | 0.0068 | 0.37 | 0.0063 |
| 19g | <0.01 | 0.074 | 0.0045 | 0.0053 | 0.0039 | 0.27 | 0.0045 |
| 19h | <0.01 | 0.17 | 0.0049 | 0.0067 | 0.0047 | 0.45 | 0.0049 |
| 19i | 2.22 | >10 | 3.2 | 4.1 | 2.9 | >10 | 2.8 |
| 20a | <0.01 | 0.47 | 0.012 | 0.0052 | 0.0031 | 0.37 | 0.0078 |

TABLE Ia

Solubilities of some of the synthetic modifications, human cancer cell line growth inhibition (GI$_{50}$ μg/mL) and murine P388 lymphocytic leukemia inhibitory activity (ED$_{50}$μg/ml).

| Compound | Solubility[a] (mg/mL) | Leukemia P388 | Pancreas BXPC-3 | Breast MCF-7 | CNS SF268 | Lung-NSC NCI-H460 | Colon KM20L2 | Prostate DU-145 |
|---|---|---|---|---|---|---|---|---|
| A | — | 0.0003 | 0.39 | — | <0.001 | 0.0006 | 0.061 | 0.0048 |
| B | — | 0.0004 | — | — | 0.036 | 0.029 | 0.034 | — |
| C | — | 0.26 | 2.3 | 0.49 | 0.0083 | 0.19 | 1.2 | 0.0043 |
| D | — | 0.0020 | 0.745 | 0.0027 | 0.0016 | 0.0032 | >1 | 0.019 |
| E | — | 0.0020 | 0.048 | 0.00022 | 0.00018 | 0.00029 | 0.328 | 0.00018 |
| F | — | 0.189 | 2.7 | 0.18 | 0.55 | 0.21 | 1.7 | 0.27 |
| G | — | 0.0028 | 0.038 | 0.0027 | 0.0036 | 0.0034 | 0.15 | 0.0021 |
| H | — | >10 | 3.0 | 0.94 | 3.3 | 3.4 | >10 | 5.8 |
| I | — | 0.0089 | 0.040 | 0.00053 | 0.0023 | 0.0032 | 0.075 | 0.0020 |
| J | — | 0.022 | 0.080 | <0.0001 | 0.0002 | 0.00031 | 0.16 | 0.00026 |
| K | 14 | 0.0021 | 0.381 | 0.0064 | 0.0057 | 0.0043 | >1 | 0.0038 |
| L | 2 | 0.0020 | 0.469 | 0.018 | 0.018 | 0.017 | >1 | 0.011 |
| M | ≧2.4 | 0.017 | 0.490 | 0.0038 | 0.0040 | 0.0039 | >1 | 0.0043 |
| N | — | 0.0032 | 0.21 | 0.0047 | 0.0037 | 0.0036 | 0.24 | 0.0026 |
| O | ≧4 | 0.0026 | 0.32 | 0.0065 | 0.0044 | 0.0036 | 0.51 | 0.0029 |
| P | ≧2 | 0.0026 | 0.16 | 0.0044 | 0.0033 | 0.0031 | 0.32 | 0.0021 |
| Q | — | 0.0022 | 0.26 | 0.035 | 0.0097 | 0.0034 | 0.59 | 0.0030 |
| R | — | 0.0029 | 0.37 | 0.0048 | 0.0043 | 0.0040 | 0.40 | 0.0047 |
| S | 22 | 0.0034 | 0.44 | 0.050 | 0.053 | 0.046 | >1 | 0.028 |
| T | 2 | 0.030 | >1 | 0.066 | 0.051 | 0.327 | >1 | 0.242 |
| U | ≧4 | 0.021 | 0.37 | 0.051 | 0.050 | 0.050 | >1 | 0.032 |
| V | — | 0.014 | 0.35 | 0.066 | 0.054 | 0.033 | >1 | 0.028 |
| W | — | 0.011 | 0.33 | 0.070 | 0.041 | 0.025 | >1 | 0.025 |
| X | — | 0.011 | 0.36 | 0.10 | 0.054 | 0.030 | >1 | 0.023 |

TABLE Ia-continued

Solubilities of some of the synthetic modifications, human cancer cell line growth inhibition ($GI_{50}$ μg/mL) and murine P388 lymphocytic leukemia inhibitory activity ($ED_{50}$ μg/ml).

| Compound | Solubility[a] (mg/mL) | Leukemia P388 | Pancreas BXPC-3 | Breast MCF-7 | CNS SF268 | Lung-NSC NCI-H460 | Colon KM20L2 | Prostate DU-145 |
|---|---|---|---|---|---|---|---|---|
| Y | — | 0.017 | 0.37 | 0.22 | 0.086 | 0.033 | >1 | 0.026 |
| Z | — | 0.026 | 0.33 | 0.047 | 0.040 | 0.025 | 0.94 | 0.021 |

[a]Solubility values were obtained using 1 mL $D_2O$ at 25° C.

Key to Table Ia
A = combretastatin A-4
B = sodium combretastatin A-4 phosphate
C = combretastatin A3
D = fluorocombstatin
E = 3-Iodo-4,4',5-trimethoxy-3'-hydroxy-Z-stilbene
F = 3-Iodo-4,4',5-trimethoxy-3'-hydroxy-E-stilbene
G = 3,5-diiodo-4,4'-dimethoxy-3'-hydroxy-Z-stilbene
H = 3,5-diiodo-4,4'-dimethoxy-3'-hydroxy-E-stilbene
I = 3,5-diiodo-4,4'-dimethoxy-3'-acetyl-Z-stilbene
J = 3-iodo-4,4',5-trimethoxy-3'acetyl-Z-stilbene
K = Potassium 3-iodo, 4,4',5 trimethoxy-Z-stilbene 3'-O-phosphate
L = Sodium 3-iodo-4,4',5-trimethoxy-Z-stilbene 3'-O-phosphate
M = Lithium 3 iodo-4,4',5-trimethoxy-Z-stilbene 3'-O-phosphate
N = Morpholine 3-iodo-4,4',5-trimethoxy-Z-stilbene 3'-O-phosphate
O = Piperidine 3-iodo-4,4',5-trimethoxy-Z-stilbene 3'-O-phosphate
P = Glycine-O-Me-3-iodo, 4,4',5-trimethoxy-Z-stilbene-3'-O-phosphate
Q = Tryptophan-O-Me-3-iodo-4,4',5-trimethoxy-Z-stilbene 3'-O-phosphate
R = Tris-iodo-4,4',5-trimethoxy-Z-stilbene 3'-O-phosphate
S = Potassium 3,5-diiodo-4,4' dimethoxy-Z-stilbene 3'-O-phosphate
T = Sodium 3,5-diiodo-4,4'-dimethoxy-Z-stilbene 3'-O-phosphate
U = Lithium 3,5-diiodo-4,4' dimethoxy-Z-stilbene 3'-O-phosphate
V = Morpholine 3,5-diiodo-4,4' dimethoxy-Z-stilbene 3'-O-phosphate
W = Piperidine 3,5-diiodo-4,4' dimethoxy-Z-stilbene 3'-O-phosphate
X = Glycine-O-Me 3,5-diiodo-4,4' dimethoxy-Z-stilbene 3'-O-phosphate
Y = Tryptophan-OMe-3,5-diiodo-4,4' dimethoxy-Z-stilbene 3'-O-phosphate
Z = Tris 3,5 diiodo-4,4' dimethoxy-Z-stilbene 3'-O-phosphate

TABLE II

Inhibition of tubulin polymerization and binding of [$^3$H]colchicine to tubulin by halocombstatins

| Compound | Inhibition of polymerization $IC_{50}$ (μM) ± S.D. | Inhibition of colchicine binding % inhibition ± S.D. |
|---|---|---|
| 1a | 1.8 ± 0.2 | 81 ± 3 |
| 11a | 1.5 ± 0.2 | 75 ± 6 |
| 12a | 1.6 ± 0.3 | 85 ± 4 |
| 13a | 1.5 ± 0.2 | 89 ± 2 |
| 14a | 1.6 ± 0.2 | 84 ± 7 |

TABLE III

Antimicrobial activities of halocombstatins and other compounds Range of minimum inhibitory concentration (μg/ml)

| Microorganism | 11a | 11b | 12a | 14a | 14b | 13a | 13b | 18a | 20a |
|---|---|---|---|---|---|---|---|---|---|
| Cryptococcus neoformans | 64 | 64 | 64 | 32-64 | 64 | * | * | * | * |
| Candida albicans | * | * | * | * | * | * | * | * | * |
| Staphylococcus aureus | * | 32-64 | * | * | 8-64 | * | * | * | * |
| Streptococcus pneumoniae | 64 | 64 | 32-64 | 64 | * | * | * | * | * |
| Enterococcus faecalis | * | * | * | * | * | * | * | * | * |
| Micrococcus luteus | 32-64 | 16-32 | 32 | 16-32 | 4-8 | 32-64 | * | * | * |
| Escherichia coli | * | * | * | * | * | * | * | * | * |
| Enterobacter cloacae | * | * | * | * | * | * | * | * | * |
| Stenotrophomonas maltophilia | * | * | * | * | * | * | * | * | * |
| Neisseria gonorrhoeae | 32 | 8-16 | 16 | 16-32 | 4-16 | 32-64 | * | 16 | 16-32 |

* = no inhibition at 64 μg/ml

TABLE IV

Human Anaplastic Thyroid Carcinoma Cell Line Inhibition Values ($GI_{50}$) expressed in µg/mL.

| Compound | KAT-4 | SW1736 |
|---|---|---|
| 3-Iodo-4,4',5-trimethoxy-3'-hydroxy-Z-stilbene | 0.089-0.14 | 2.2 |
| 3,5-diiodo-4,4'-dimethoxy-3'-hydroxy-Z-stilbene | 0.039-0.063 | 1.2 |
| Potassium 3-iodo-4,4',5-trimethoxy-Z-stilbene 3'-O-phosphate | 0.37-0.43 | >10 |
| Potassium 3,5-diiodo-4,4'dimethoxy-Z-stilbene 3'-O-phosphate | 0.38-0.44 | >10 |

TABLE V

Human Umbilical Vein Endothelial Cell (HUVEC) Inhibition Values ($GI_{50}$) expressed in µg/mL.

| Compound | HUVEC |
|---|---|
| 3-Iodo-4,4',5-trimethoxy-3' hydroxyl-Z-stilbene | 0.000040 |
| 3,5-diiodo-4,4'-dimethoxy-3'-hydroxy-Z-stilbene | 0.00028 |
| Potassium 3-iodo-4,4',5-trimethoxy-Z-stilbene 3'-O-phosphate | 0.00025 |
| Sodium 3-iodo-4,4',5-trimethoxy-Z-stilbene 3'-O-phosphate | 0.00035 |
| Potassium 3,5-diiodo-4,4' dimethoxy-Z-stilbene 3'-O-phosphate | 0.0049 |
| Sodium 3,5-diiodo-4,4' dimethoxy-Z-stilbenes 3'-O-phosphate | 0.051 |

TABLE VI

Length of Cords Formed, Number of Junctions and Relative Percent Growth

| | Drug concentration | Lengths of Cords | Number of junctions | Relative % Growth |
|---|---|---|---|---|
| 3-Iodo-4,4',5-trimethoxy-3'-hydroxy-Z-stilbene | 0.01 µg/ml | − | − | 14 |
| | 0.001 µg/ml | + | + | 14 |
| | 0.0001 µg/ml | ++(+) | ++(+) | 18 |
| | 0.00001 µg/ml | | | 90 |
| 3,5-diiodo-4,4' dimethoxy-3'-hydroxy-Z-stilbene | 0.01 µg/ml | − | − | 4 |
| | 0.001 µg/ml | + | (+) | 8 |
| | 0.0001 µg/ml | +++ | +++ | 84 |
| | 0.00001 µg/ml | | | 87 |
| Potassium 3-iodo-4,4',5-trimethoxy-Z-stilbene-3'-O-phosphate | 0.01 µg/ml | | | 1 |
| | 0.001 µg/ml | ++ | ++(+) | 10 |
| | 0.0001 µg/ml | +++ | +++ | 77 |
| | 0.00001 µg/ml | +++ | +++ | 95 |
| Sodium 3-iodo-4,4',5-trimethoxy-z-stilbene-3'-O-phosphate | 0.1 µg/ml | − | − | 7 |
| | 0.01 µg/ml | − | − | 14 |
| | 0.001 µg/ml | + | + | 5 |
| | 0.0001 µg/ml | | | 104 |
| Potassium 3,5-diiodo-4,4' dimethoxy-Z-stilbene 3'-O-phosphate | 0.1 µg/ml | − | − | 15 |
| | 0.01 µg/ml | ++(+) | ++(+) | 33 |
| | 0.001 µg/ml | +++ | +++ | 88 |
| | 0.0001 µg/ml | | | 96 |
| Sodium 3,5-diiodo-4,4'-dimethoxy-Z-stilbene 3'-O-phosphate | 1 µg/ml | − | − | −7 |
| | 0.1 µg/ml | + | (+) | −2 |
| | 0.01 µg/ml | ++(+) | ++(+) | >100 |
| | 0.0001 µg/ml | | | >100 |

| Legend | Lengths of Cords | Number of junctions |
|---|---|---|
| − | No Cords | No Junctions |
| + | Small | Few |
| ++ | ~50% of Control | ~50% of Control |
| +++ | Same as Control | Same as Control |

TABLE VII

Antimicrobial activities of iodocomstatins

| Microorganism | ATCC or (Presque Isle)# | Range of MIC (µg/ml) Compound | | | | | | | | | | | | |
|---|---|---|---|---|---|---|---|---|---|---|---|---|---|
| | | A | B | C | D | E | F | G | H | I | J | K | L | M |
| Cryptococcus neoformans | 90112 | * | 64 | * | * | * | * | * | * | * | * | * | * | * |
| Candida albicans | 90028 | * | * | * | * | * | * | * | * | * | * | * | * | * |
| Staphylococcus aureus | 29213 | * | * | * | * | * | * | * | * | * | * | * | * | * |
| Streptococcus pneumoniae | 6303 | * | * | * | * | * | * | * | * | * | * | * | * | * |

TABLE VII-continued

Antimicrobial activities of iodocomstatins

| | | | | | | | | | | | | | | |
|---|---|---|---|---|---|---|---|---|---|---|---|---|---|---|
| Enterococcus faecalis | 29212 | * | * | * | * | * | * | * | * | * | * | * | * | * |
| Micrococcus luteus | (456) | * | * | 4-16 | 2-4 | * | * | * | * | * | * | * | * | * |
| Escherichia coli | 25922 | * | * | * | * | * | * | * | * | * | * | * | * | * |
| Enterobacter cloacae | 13047 | * | * | * | * | * | * | * | * | * | * | * | * | * |
| Stenotrophomonas maltophilia | 13637 | * | * | * | * | * | * | * | * | * | * | * | * | * |
| Neisseria gonorrhoeae | 49226 | 64 | * | * | * | * | * | * | * | 16-32 | * | * | 4-8 | 32-64 |

| | | Range of MIC (μg/ml) Compound | | | | | | | |
|---|---|---|---|---|---|---|---|---|---|
| Microorganism | ATCC or (Presque Isle)# | N | O | P | Q | R | S | T | U |
| Cryptococcus neoformans | 90112 | * | * | * | * | * | * | * | * |
| Candida albicans | 90028 | * | * | * | * | * | * | * | * |
| Staphylococcus aureus | 29213 | * | * | * | * | * | * | * | * |
| Streptococcus pneumoniae | 6303 | * | * | * | * | * | * | * | * |
| Enterococcus faecalis | 29212 | * | * | * | * | * | * | * | * |
| Micrococcus luteus | (456) | * | * | * | * | * | * | * | * |
| Escherichia coli | 25922 | * | * | * | * | * | * | * | * |
| Enterobacter cloacae | 13047 | * | * | * | * | * | * | * | * |
| Stenotrophomonas maltophilia | 13637 | * | * | * | * | * | * | * | * |
| Neisseria gonorrhoeae | 49226 | <0.5-4 | 32-64 | <0.5-2 | <0.5 | <0.5 | <0.5-1 | <0.5 | <0.5-2 |

Key for Table VII
B 3-iodo-4,4'5-trimethoxy-3'-hydroxy-Z-stilbene
C 3,5-diiodo-4,4'-dimethoxy-3' hydroxy-Z-stilbene
D 3,5-diiodo-4,4'-dimethoxy-3' hydroxy-E-stilbene
E 3,5-diiodo-4,4'-dimethoxy-3'-acetyl-Z-stilbene
F Potassium 3 iodo-4,4'5-trimethoxy-Z-stilbene 3'-O-phosphate
G Sodium 3 iodo-4,4',5 trimethoxy-Z-stilbene-3'-O-phosphate
H Lithium-3-iodo-4,4'5 trimethoxy-Z-stilbene 3'O-phosphate
I Morpholine 3 iodo-4,4'5-trimethoxy-Z-stilbene-3'-O phosphate
J Piperidene 3-iodo-4,4',5-trimethoxy-Z-stilbene-3'O phosphate
K Glycine-O-Me-3-iodo-4,4',5-trimethoxy-Z-stilbene-3'-O-phosphate
L Tryptophan-O-Me-3'-iodo-4,4',5 trimethoxy-Z-stilbene 3'-O-phosphate
M Tris-3-iodo-4,4',5-trimethoxy-Z-stilbene 3'-O-phosphate
N Potassium 3,5 diiodo-4,4' dimethoxy-Z-stilbene 3'-O-phosphate
O Sodium 3,5-diiodo-4,4' dimethoxy-Z-stilbene 3'-O-phosphate
P Lithium 3,5-diiodo-4,4' dimethoxy-Z-stilbene 3'O phosphate
Q Morpholine 3,5 diiodo-4,4' dimethoxy-Z-stilbene 3-O-phosphate
R Piperdine 3,5 diiodo-4,4' dimethoxy-Z-stilbene 3'O-phosphate
S Glycine O Me 3,5-diiodo-4,4' dimethoxy-Z-stilbene-3'-O-phosphate
T Tryptophan-O Me 3,5 diiodo 4,4' dimethoxy-Z-stilbene-3'-O-phosphate
U Tris 3,5-diodo-4,4' methoxy-Z-stilbene 3'O-phosphate

What is claimed is:

1. A method for synthesizing a compound having a structure as follows:

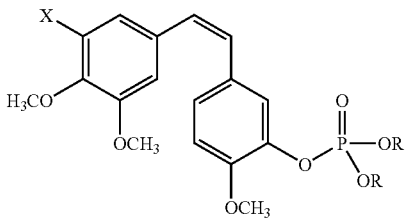

wherein X is a halogen and R is a metal selected from the group consisting of Na+, Li+, K+, Cs+, Rb+, CA2+, and Mg2+ said method comprising the following reaction steps:

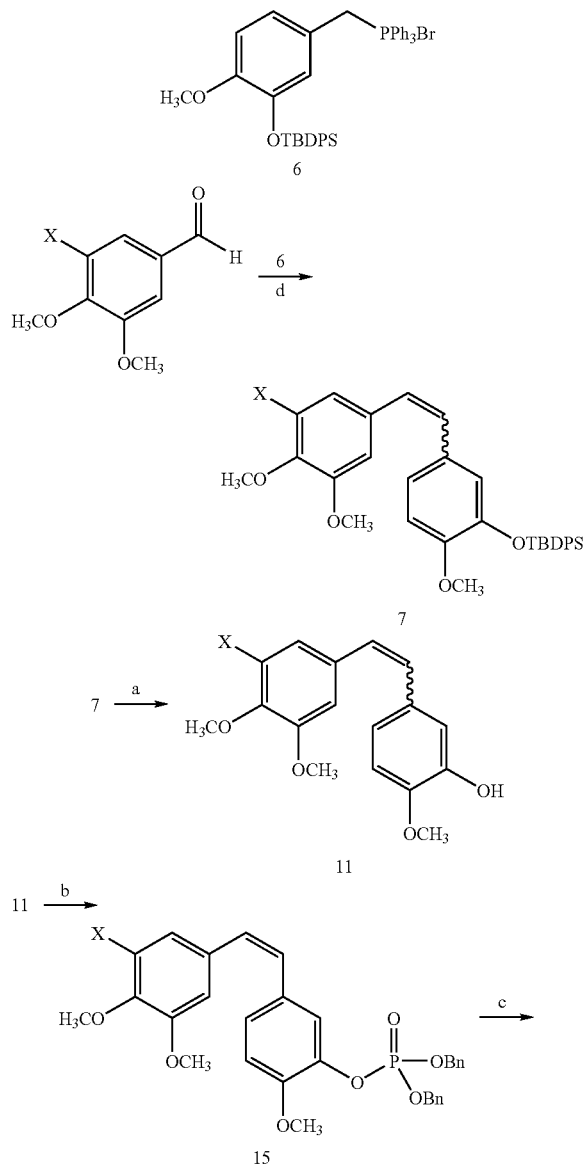

wherein
d=reacting with tetrahydrofuran and n-butyl lithium;
a=reacting the Z isomer of compound 7 with tetrahydrofuran and tetraammonium halide;
b=reacting the Z isomer of compound 11 with dibenzyl phosphite;
c=reacting compound 15 with trimethylsilyl halide, stirring, and adding a metal hydroxide, methoxide, or metal acetate.

2. The method of claim 1, wherein X is selected from the group consisting of F, Br, and I.

3. The method of claim 2, wherein step c comprises adding a hydroxide, methoxide, or acetate selected from the group consisting of hydroxides, methoxides, and acetates of Na+, Li+, K+, Cs+, Rb+, Ca2+, and Mg2+.

4. The method of claim 3, wherein step c comprises adding sodium methoxide.

5. A method for synthesizing a compound having a structure as follows:

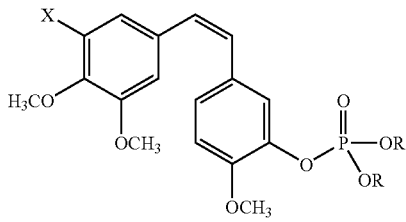

wherein X is a halogen and R is an amino group selected from the group consisting of morpholine, piperidine, glycine —OCH3, tryptophan —OCH3 and NH(CH2OH)3, said method comprising the following reaction steps:

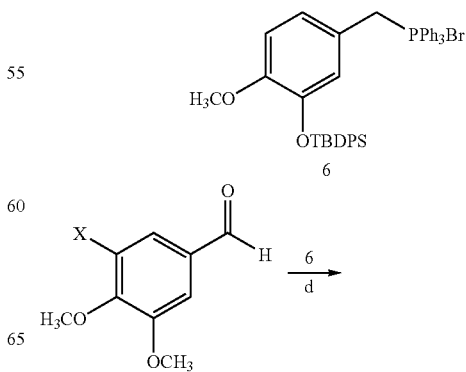

37

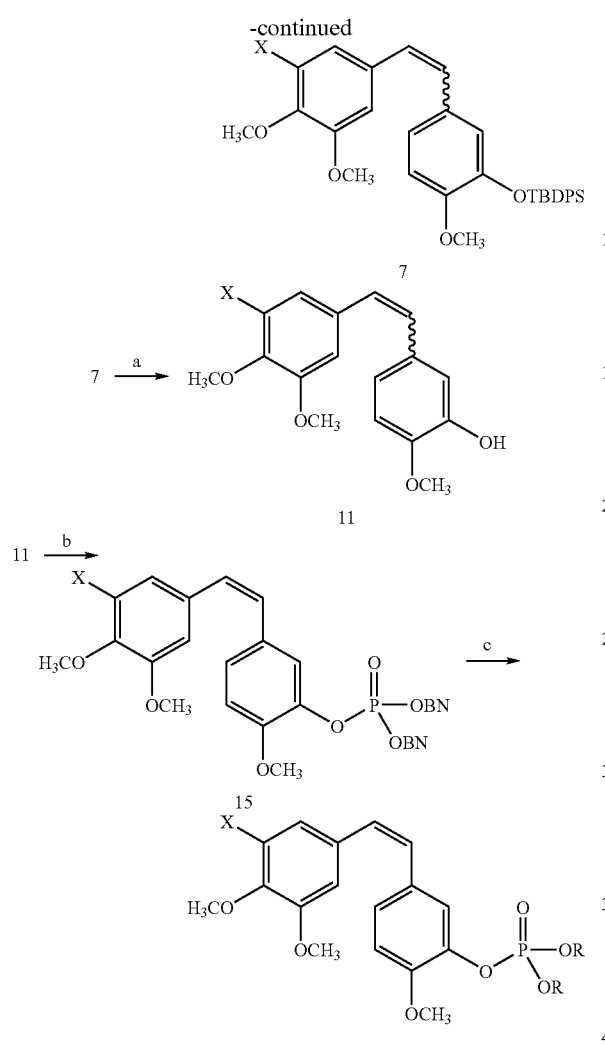

wherein
- d=reacting with tetrahydrofuran and n-butyl lithium;
- a=reacting the Z isomer of compound 7 with tetrahydrofuran and tetraammonium halide;
- b=reacting the Z isomer of compound 11 with dibenzyl phosphite;
- c=applying compound 15 to a resin column hearing an amine or amino acid ester selected from the group consisting of morpholine, piperidine, glycine —OCH₃, tryptophan —OCH₃ and NH(CH₂OH₃).

6. A method for synthesizing a compound having a structure as follows:

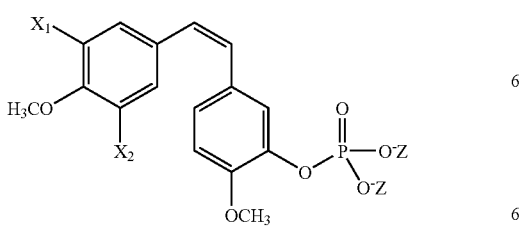

38 wherein $X_1$ and $X_2$ are each a halogen and Z is a metal selected from the group consisting of Na⁺, Li⁺, K³⁰, Cs⁺, Rb⁺, Ca²⁺ and Mg²⁺, said method comprising the following reaction steps:

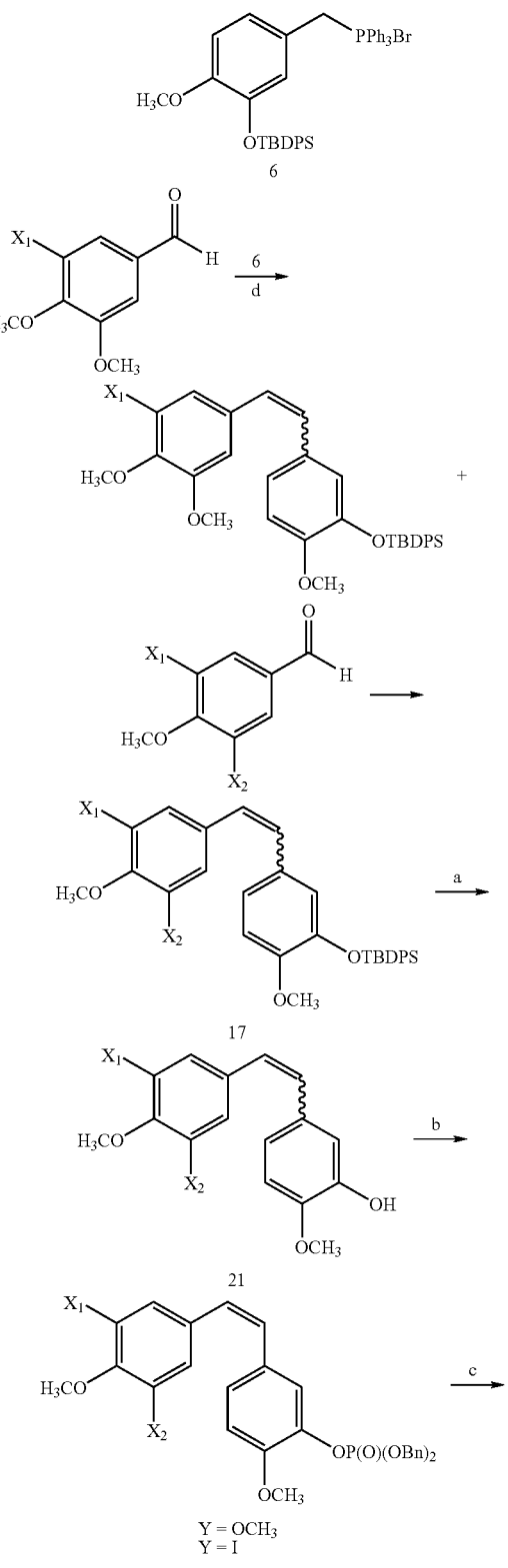

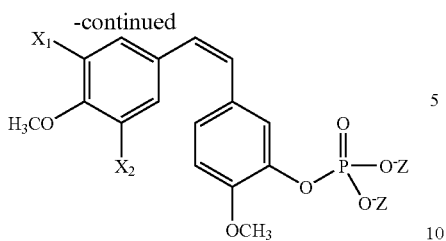

wherein
- d=reacting with tetrahydrofuran and n-butyl lithium;
- a=reacting the Z isomer of compound 17 with tetrahydrofuran and tetraammonium halide;
- b=reacting the Z isomer of compound 21 with dibenzyl phosphite;
- c=reacting compound 25 with trimethylsilyl halide, stirring and adding a metal hydroxide, methoxide or metal acetate.

7. The method of claim 6, wherein $X_1$ and $X_2$ are selected from the group consisting of F, Br and I.

8. The method of claim 7, wherein c comprises adding a hydroxide, methoxide, or metal acetate selected from the group consisting of hydroxides, methoxides, and acetates of $Na^+$, $Li^+$, $K^+$, $Cs^+$, $Rb^+$, $Ca^{2+}$ and $Mg^{2+}$.

9. The method of claim 7, wherein c comprises adding sodium methoxide and $X_1$ and $X_2$ are each iodine.

10. A method for synthesizing a compound having a structure as follows:

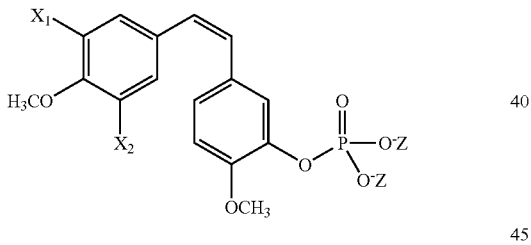

wherein $X_1$ and $X_2$ are each a halogen and Z is a metal selected from the group consisting of $Na^+$, $Li^+$, $K^+$, $Cs^+$, $Rb^+$, $Ca^{2+}$, and $Mg^{2+}$ said method comprising the following reaction steps:

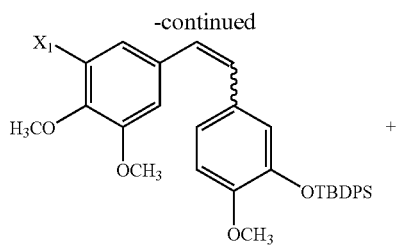

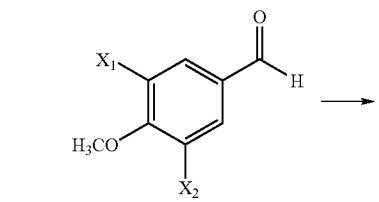

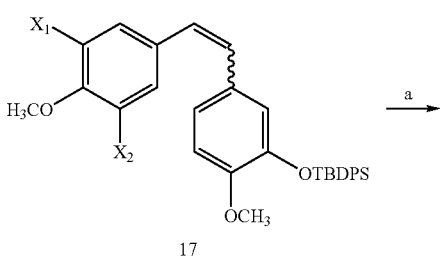

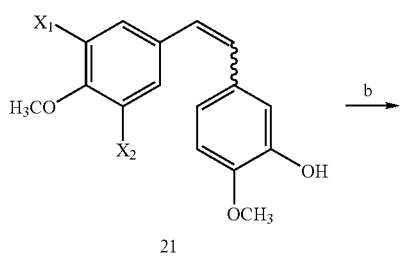

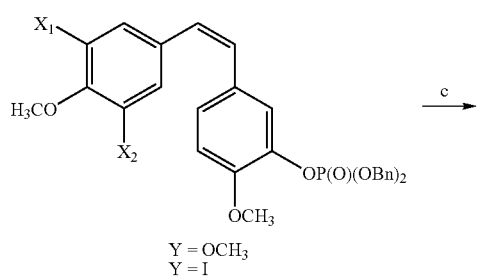

wherein
- d=reacting with tetrahydrofuran and n-butyl lithium;
- a=reacting the Z isomer of compound 17 with tetrahydrofuran and tetraammonium halide;
- b=reacting the Z isomer of compound 21 with dibenzyl phosphite;
- c=applying compound 25 to a resin column bearing an amine or amino acid ester selected from the group consisting of morpholine, piperidine, glycine —$OCH_3$, trytophan —$OCH_3$ and $NH(CH_2OH_3)$.

11. The method of claim 10, wherein $X_1$ and $X_2$ are selected from the group consisting of F, Br and I.

12. The method of claim 11, wherein $X_1$ and $X_2$ are each iodine.

* * * * *